US006083986A

United States Patent [19]
Castle et al.

[11] Patent Number: 6,083,986
[45] Date of Patent: Jul. 4, 2000

[54] POTASSIUM CHANNEL INHIBITORS

[75] Inventors: Neil Alexander Castle, Cary; Sean Patrick Hollinshead, Durham; Philip Floyd Hughes, Chapel Hill; Jose Serafin Mendoza; Joseph Wendell Wilson, both of Durham; George Salvatore Amato, Cary; Serge Beaudoin, Morrisville; Michael Gross, Durham; Grant McNaughton-Smith, Morrisville, all of N.C.

[73] Assignees: ICAgen, Inc., Durham, N.C.; Eli Lilly & Company, Indianapolis, Ind.

[21] Appl. No.: 08/893,160

[22] Filed: Jul. 15, 1997

Related U.S. Application Data

[60] Provisional application No. 60/022,547, Jul. 26, 1996.

[51] Int. Cl.[7] .......................... A61K 31/17; A61K 31/18; A61K 31/216; A61K 31/4155
[52] U.S. Cl. .......................... 514/586; 514/354; 514/378; 514/448; 514/471; 514/521; 514/439; 514/551; 514/596; 514/597; 514/602; 514/604; 546/314; 546/323; 548/248; 549/72; 549/487; 558/404; 560/13; 560/255; 564/27; 564/49; 564/84; 564/91
[58] Field of Search .................................. 564/27, 49, 84, 564/91; 514/586, 597, 602, 604, 354, 378, 448, 471, 521, 539, 551, 596; 548/248; 546/323, 314; 549/72, 487; 558/404; 560/13, 255

[56] References Cited

U.S. PATENT DOCUMENTS

| | | | |
|---|---|---|---|
| 2,298,443 | 10/1942 | Weissberger | 564/91 |
| 4,422,871 | 12/1983 | Schirmer et al. | 564/49 |
| 4,975,453 | 12/1990 | Becker et al. | 514/456 |
| 5,006,512 | 4/1991 | Ohnishi | 514/21 |
| 5,215,985 | 6/1993 | Murphy et al. | 514/212 |
| 5,234,947 | 8/1993 | Cherksey | 514/449 |
| 5,242,947 | 9/1993 | Cherksey et al. | 514/628 |
| 5,310,932 | 5/1994 | Atwal et al. | 548/454 |
| 5,328,830 | 7/1994 | Janis et al. | 435/7.21 |
| 5,356,775 | 10/1994 | Herbert et al. | 435/6 |
| 5,401,758 | 3/1995 | Atwal et al. | 514/353 |
| 5,401,848 | 3/1995 | Atwal | 546/153 |
| 5,451,580 | 9/1995 | Murphy et al. | 514/212 |
| 5,453,421 | 9/1995 | Atwal et al. | 514/100 |
| 5,486,515 | 1/1996 | Brown et al. | 514/229.8 |

FOREIGN PATENT DOCUMENTS

| | | |
|---|---|---|
| 0 286 278 | 10/1988 | European Pat. Off. . |
| 0 317 321 | 5/1989 | European Pat. Off. . |
| 0 321 175 | 8/1989 | European Pat. Off. . |
| 0 472 053 | 2/1992 | European Pat. Off. . |
| 0 488 616 | 6/1992 | European Pat. Off. . |
| 0 587 180 | 3/1994 | European Pat. Off. . |
| 0 608 858 | 8/1994 | European Pat. Off. . |
| WO 95/18617 | 7/1995 | WIPO . |
| 95/26342 | 10/1995 | WIPO . |
| 96/21640 | 7/1996 | WIPO . |
| 96/36596 | 11/1996 | WIPO . |
| 97/25893 | 7/1997 | WIPO . |
| 97/25983 | 7/1997 | WIPO . |
| 97/26300 | 7/1997 | WIPO . |

OTHER PUBLICATIONS

Still, et al., "Rapid Chromatographic Technique for Preparative Separation with Moderate Resolution," J. Org. Chem., vol. 43, No. 14, 1978, 2923–2925.

Castle, et al., "Characterization of 4–Aminopyridne Block of the Transient Outward K[+] Current in Adult Rat Ventricular Myocytes," The Journal of Pharmacology and Experimental, vol. 264, No. 3, 1450–1459 (1993).

Deal, et al., "Molecular Physiology of Cardiac Potassium Channels," Physiological Reviews, vol. 76, No. 1, Jan. 1996, 49–67.

Wang, et al, "Sustained Depolarization–Induced Outward Current in Human Atrial Myocytes, Evidence for a Novel Delayed Rectified K[+] Current Similar to Kv1.5 Cloned Channel Current," Circulation Research, vol. 73, No. 6, Dec. 1993, 1061–1076.

Hamill, "Improved Patch–Clamp Techniques for High––Resolution Current Recording from Cells and Cell–Free Membrane Patches," Pflüger Archiv, (1981) 391:85–100.

Fedida, et al., "Identity of a Novel Delayed Rectifier Current From Human Heart With a Cloned K[+] Channel Current," Circulation Research, vol. 73, No. 1, Jul. 1993, 210–216.

Chandy, et al., "Voltage–Gated Potassium Channels Are Required For Human T. Lymphocyte Activation," J. Exp. Med., vol. 160, Aug. 1984, 369–385.

Sanguinetti, "Modulation of Potassium Channels by Antiarrhythmic and Antihypertensive Drugs," Hypertension, vol. 19, No. E, Mar. 1992, 228–236.

Lynch, et al., "Therapeutic Potential of modulating Potassium Currents in the Diseased Myocardium," The FASEB Journal, vol. 6, Aug. 1992, 2952–2960.

Colatsky, et al, "Channel Specificity in Antiarrhythmic Drug Action," Circulation, vol. 82, No. 6, Dec. 1990, 2235–2242.

Halliwell, "K[+] Channels in the Central Nervous System," 348–381 (1988).

Amos, et al. "Differences Between Outward Currents of Human Atrial and Subepicardial Ventricular Myocytes," Journal of Physiology, (1986), 491.1, 31–50.

Wang, et al., "Effects of Flecanide, Quinidine, and 4–Aminopyridine on Transient Outward and Ultrarapid Delayed Rectifier Currents in Human Atrial Myocytes," The Journal of Pharmacology and Experiemental Therapeutics, vol. 272, No. 1, 184–196 (1995).

Lin, et al., Voltage–gated Potassium Channel Regulate Calcium–dependent Pathways Involved in Human T Lymphocyte Activation, J. Exp. Med., vol. 177, 637–645 (1993).

Kaczorowki, et al., "lymphocyte Ion Channels as a Target for Immunosuppression," Perspective in Drug Discovery and Design 2 (1994) 233–248.

(List continued on next page.)

*Primary Examiner*—Peter O'Sullivan
*Attorney, Agent, or Firm*—Banner & Witcoff, Ltd.

[57] ABSTRACT

Compounds useful as potassium channel inhibitors and especially useful for the treatment of cardiac arrhythmias and cell proliferative disorders are described.

23 Claims, 5 Drawing Sheets

OTHER PUBLICATIONS

Leonard, et al., Selective Blockers of voltage–Gated $K^+$ Channels Depolarize Human T Lymphocytes: Mechanism of the Antiproliferative Effect of Charybdotoxin, vol. 89, 10094–10098, Nov. 1992.

Doupnik, et al., "The Inward Rectifier Potassium Channel Family," Current Opinion in Neurobiology, 1995, 5:268–277.

Chandy, et al., "Voltage–Gated Potassium Channel Genes," Handbook of Receptors and Channels, 1–71 (1995).

Epps et al., Chemistry and Physics of Lipids, 69(1994) pp. 137–150.

WO 95–18617 Abstract (1995).

Chem. Abs., vol. 104, No. 9 Abs No. 68632 (Mar. 3, 1986).

International Search Report PCT/US97/12559 (1997).

POTASSIUM CHANNEL INHIBITORS

BACKGROUND OF THE INVENTION

This application claims priority benefits under 35 U.S.C. 119 of provisional application No. 60/022,547 filed Jul. 26, 1996.

1. Field of the Invention

The present invention is broadly directed to a class of compounds useful as potassium channel inhibitors.

2. Description of Related Art

Potassium channels, as a class of channels, are ubiquitously expressed in eukaryotic and procaryotic cells, and are key elements in the control of electrical and nonelectrical cellular functions. Subclasses of these channels have been named based on amino acid sequence and functional properties, and include for example voltage gated potassium channels (e.g., Kv1, Kv2, Kv3, Kv4) and inward rectifier potassium channels (e.g., Kir1, Kir2, Kir3, Kir4, Kir5, Kir6). Subtypes within these subclasses have been characterized as to their putative function, pharmacology and distribution in cells and tissues (Chandy and Gutman, "Voltage-gated potassium channel genes" in Handbook of Receptors and Channels-Ligand and Voltage-gated Ion Channels, ed. R. A. North, 1995; Doupnik et al., *Curr. Opin. Neurobiol* 5:268, 1995).

Inhibitors of potassium channels lead to a decrease in potassium ion movement across cell membranes. Consequently, such inhibitors induce prolongation of the electrical action potential or membrane potential depolarization in cells containing the inhibited or blocked potassium channels. Prolonging of the electrical action potential is a preferred mechanism for treating certain diseases, e.g., cardiac arrhythmias (Colatsky et al., *Circulation* 82:2235, 1990). Membrane potential depolarization is a preferred mechanism for the treating of certain other diseases, such as those involving the immune system (Kaczorowski and Koo, *Perspectives in Drug Discovery and Design*, 2:233, 1994).

In particular, blocking potassium channels has been shown to regulate a variety of biological processes including cardiac electrical activity (Lynch et al., *FASEB J.* 6:2952, 1992; Sanguinetti, *Hypertension* 19: 228, 1992; Deal et al., *Physiol. Rev.* 76:49, 1996), neurotransmission (Halliwell, "K$^+$ channels in the central nervous system" in Potassium Channels, Ed. N. S. Cook, pp348, 1990), and T cell activation (Chandy et al., *J. Exp. Med.* 160:369, 1984; Lin et al., *J. Exp Med.* 177:637, 1993). These effects are mediated by specific subclasses or subtypes of potassium channels.

We have cloned and expressed various types of potassium channels which show the functional, pharmacological and tissue distribution characteristics which would make them candidate potassium channel targets for the treatment of diseases. For example, the delayed rectifier voltage-gated potassium channel termed $I_{Kur}(I_{sus})$ which has been reported to contain the Kv1.5 α-subunit gene product is generally believed to be important in the repolarization of the human atrial action potential and thus is a candidate potassium channel target for the treatment of cardiac arrhythmias especially those occurring in the atria (Wang et al., *Circ. Res.* 73:1061, 1993; Fedida et al., *Circ. Res.* 73:210, 1993; Wang et al., *J. Pharmacol. Exp. Ther.* 272:184, 1995; Amos et al., *J. Physiol.*, 491:31, 1996). Likewise, $I_{Kn}$ (which comprises the Kv1.3 α-subunit gene product) determines resting membrane potential in human T lymphocytes (Leonard et al., *Proc. Natl. Acad. Sci.* 89:10094, 1992; Kaczorowski and Koo, *Perspectives in Drug Discovery and Design*, 2:233, 1994) and thus is a candidate potassium channel target for the prevention of T cell activation in the immune response in immune-reactive conditions (Lin et al., *J. Exp Med.* 177:637, 1993).

The present invention is related to compounds which are useful as inhibitors of potassium channel function. The compounds of the invention are especially active as inhibitors of voltage-gated potassium channels. The potassium channel inhibitors of the invention may therefore be utilized for the treatment of diseases in which prolongation of cellular action potentials would be beneficial, which include, but are not limited to, cardiac arrhythmias. In addition, compounds of the invention may be utilized for treating disorders in which induction of cell membrane depolarization would be beneficial, which include, but are not limited to, cell proliferative disorders.

It is an object of the present invention, therefore, to provide compounds which are useful for the treatment of diseases in mammals, including humans, and especially for the management of diseases which can be treated by inhibiting cell membrane potassium channels, such as the potassium channels responsible for cardiac $I_{Kur}$ potassium current, or the potassium channels responsible for T-lymphocyte $I_{Kn}$ potassium current, and potassium channels containing one of Kv1.5 or Kv1.3 α-subunit gene products.

Another object of the invention is to provide a method of treating diseases in mammals, including humans, which respond to the inhibition of potassium channel function, which method comprises administering to a mammal in need thereof a compound of the invention.

DETAILED DESCRIPTION OF THE INVENTION

Figure 1:
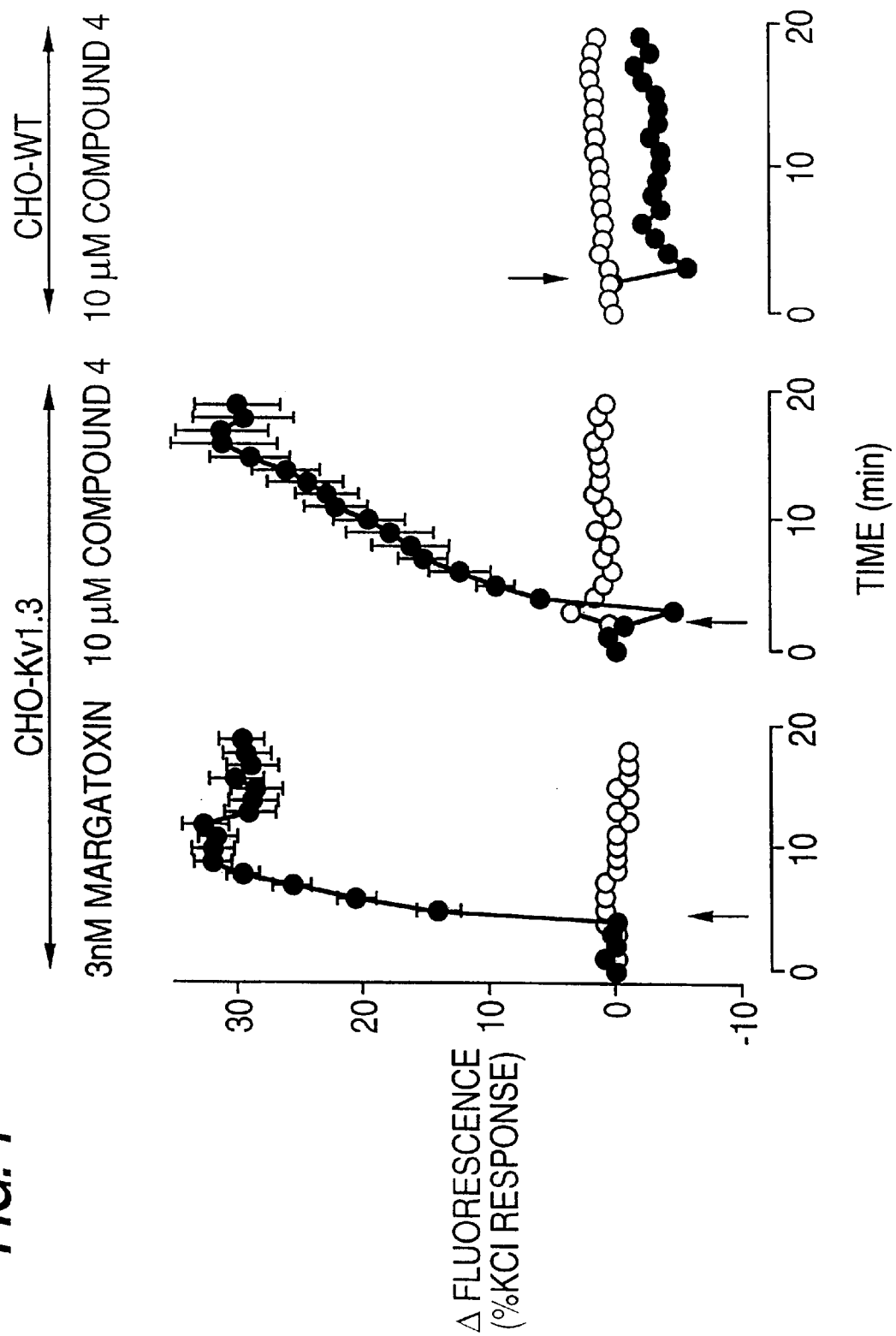
FIG. 1 compares the effect of 3 nM margatoxin and 10 μM of 1-(p-ethylphenyl)sulfimide-2-hydroxy-6-(m-methoxy)benzamido-indane, (compound 4), on membrane potential in Chinese hamster ovary (CHO) cells expressing human Kv1.3 potassium channels (CHO-Kv1.3). The effect of 10 μM of compound 4 on membrane potential in non-transfected CHO cells (CHO-WT) is also shown.

This invention describes compounds and their utility as inhibitors of voltage-dependent potassium channel function, particularly potassium channels (i.e., $I_{Kur}$, Kv1.5) that could serve as targets for the treatment of cardiac arrhythmias especially those occurring in the atria (e.g., atrial flutter and atrial fibrillation) (Wang et al., *Circ. Res.* 73:1061, 1993;

Fedida et al., *Circ. Res.* 73:210, 1993; Wang et al., *J. Pharmacol. Exp. Ther.* 272:184, 1995), as well as the potassium channels (i.e., $I_{Kn}$, Kv1.3) that could serve as targets for the treatment of immunologic diseases (Kaczorowski and Koo, *Perspectives in Drug Discovery and Design* 2:233, 1994). Consequently, the present invention also provides a method for treating diseases which respond to the inhibition of potassium channel function such as cardiac arrhythmias and various immunologic diseases using the compounds of the invention.

The invention is particularly based on our discovery that the compounds of the following formula (I) are inhibitors of potassium channel function. In particular, these compounds have demonstrated activity against the human potassium channels/currents $I_{Kur}$, $I_{Kn}$, Kv1.5, Kv1.3. As a result, these compounds are useful in the treatment of cardiac arrhythmias and cell proliferative disorders.

Thus, in a first aspect, the present invention concerns compounds having potassium channel inhibitory activity of the formula (I):

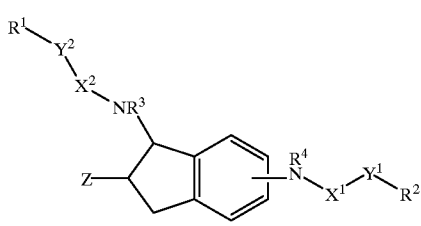

(I)

wherein, $R^1$ is H, alkyl or is selected from the group consisting of an optionally substituted aryl, an optionally substituted heteroaryl, an optionally substituted heterocyclyl and an optionally substituted carbocycloalkyl;

$R^2$ is selected from the group consisting of an alkyl, an optionally substituted aryl, an optionally substituted heteroaryl, an optionally substituted heterocyclyl and an optionally substituted carbocycloalkyl;

$R^3$ is hydrogen or methyl;
$R^4$ is hydrogen or methyl;
$X^1$ is C=O, C=S, or $SO_2$;
$X^2$ is C=O or $SO_2$;
$Y^1$ is O, $(CH_2)_p$, $CH_2O$, HC=CH or NH; wherein p is 0, 1 or 2;
$Y^2$ is O, $(CH_2)_q$, HC=CH or NH; wherein q is 0 or 1;
Z is H, $OR^5$ or $NR^6R^7$;
wherein
$R^5$ is H, $(CH_2)_m$—$R^8$; or C(O)—$(CH_2)_m$—$R^8$;
m=1 to 5;
$R^8$ is $N(R^9)_2$, $N(R^9)_3L$ or $CO_2R^9$; wherein each $R^9$ is independently selected from H or alkyl; and L is a counter ion;
$R^6$ is H or alkyl;
$R^7$ is H, alkyl or $CO_2R^{10}$; wherein $R^{10}$ is alkyl.
Suitable counter ions, L, are described below and include as non-limiting examples bromide, chloride, acetate and tosylate.

In another aspect, the present invention concerns indane compounds having potassium channel inhibition activity of the formula (II):

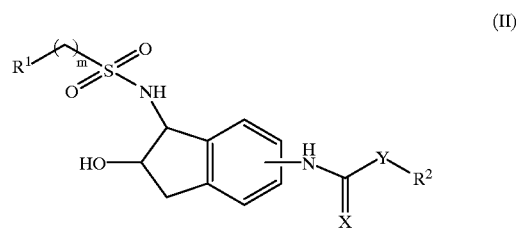

(II)

wherein, $R^1$ is H or an optionally substituted aryl selected from the group of phenyl and β-naphthyl;

$R^2$ is selected from the group of an optionally substituted phenyl, an optionally substituted heteroaryl, an optionally substituted heterocyclyl and an optionally substituted carbocycloalkyl;

m is 0 or 1;

X is O or S; and

Y is selected from one of $(CH_2)_p$, $(CH_2O)_q$ and $(NH)_r$; where p is 0, 1 or 2; q is 0 or 1, and r is 0 or 1.

Preferably, $R^2$ is phenyl per se or a phenyl substituted with one or more groups in the 2 (ortho), 3 (meta), or 4 (para) positions, wherein said groups are selected from $C_{1-6}$ alkyl, $C_{1-6}$ alkoxy, cyano, halo and trifluoromethyl. Alternatively, $R^2$ is an optionally substituted heteroaryl, an optionally substituted heterocyclyl or an optionally substituted carbocycloalkyl, wherein said optionally substituted moieties may be substituted with $C_{1-6}$ alkyl, $C_{1-6}$ alkoxy, cyano, halo and trifluoromethyl.

More preferred are compounds of the following formula (III):

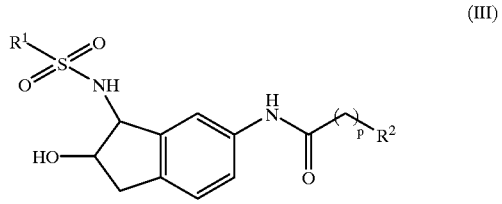

(III)

wherein, $R^1$, $R^2$ and p again have the same meanings assigned above. $R^1$ is preferably an aryl group selected from phenyl and β-naphthyl and more preferably such an aryl group substituted with groups such as $C_{1-6}$ alkyl, $C_{1-6}$ alkoxy, as well as cyano, trifluoromethyl and halo. Similarly, $R^2$ is an optionally substituted phenyl, an optionally substituted heteroaryl, an optionally substituted heterocyclyl or an optionally substituted carbocycloalkyl each of which may be substituted with $C_{1-6}$ alkyl, $C_{1-6}$ alkoxy, cyano, halo and trifluoromethyl.

Examples of molecules described under formula (I) and (II) include:

1
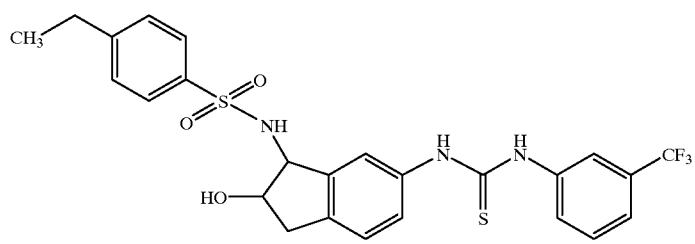
2
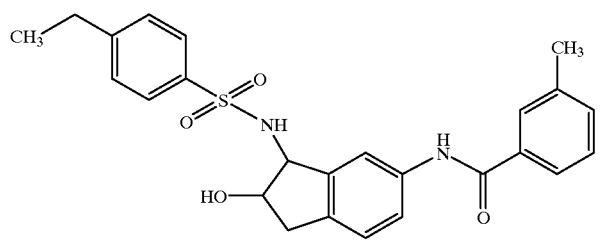
3
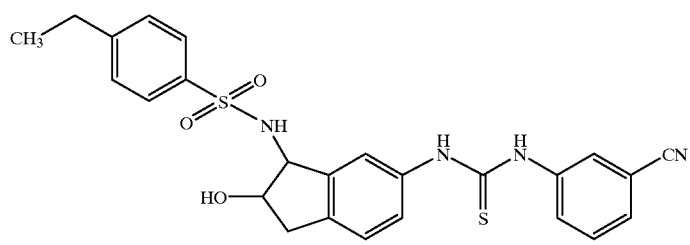
4
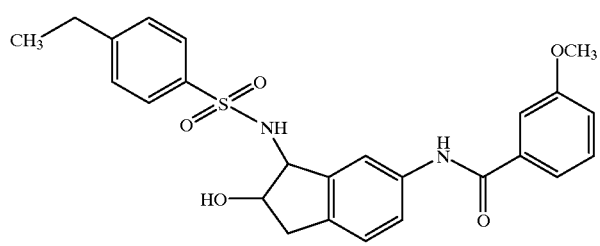
5
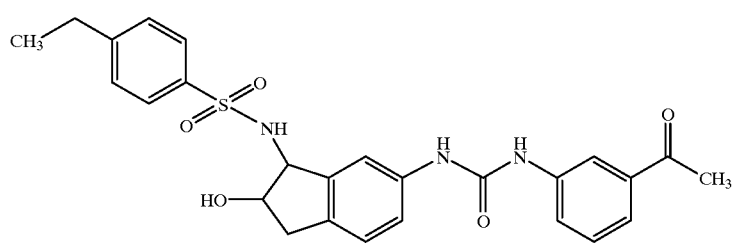
6
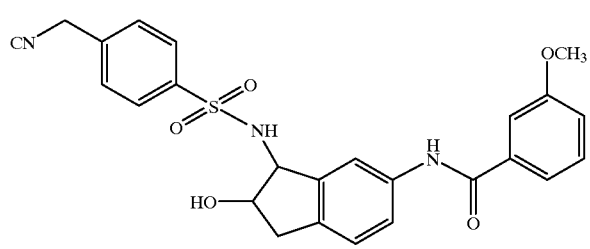

-continued
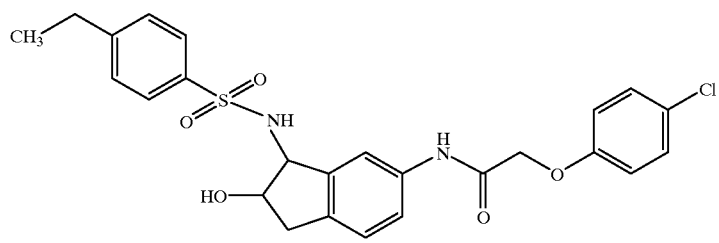
7
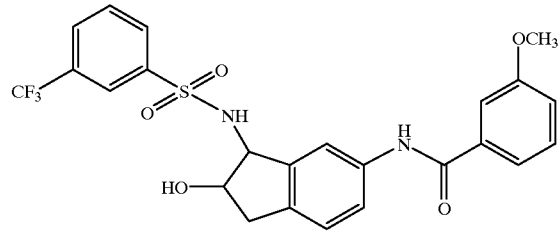
8
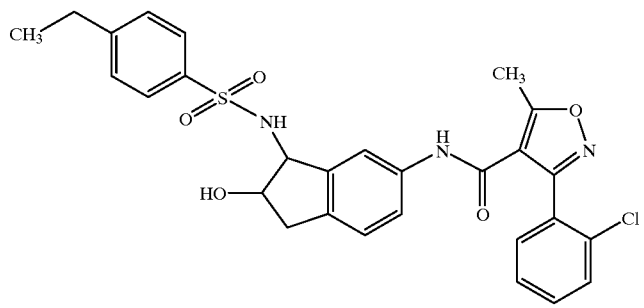
9
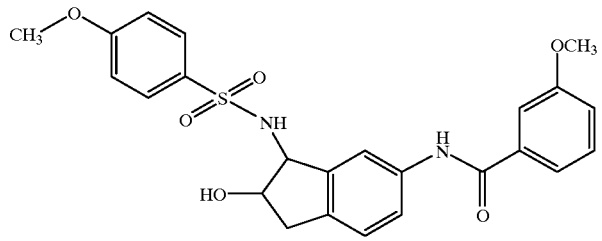
10
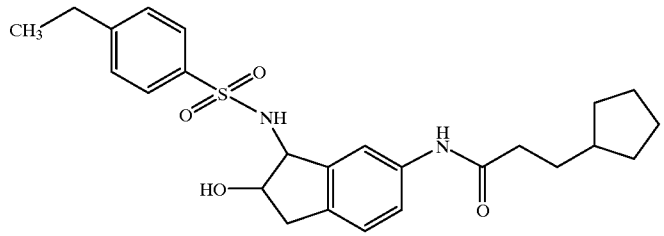
11
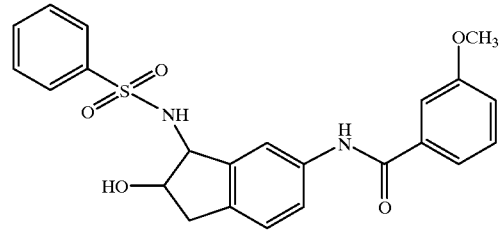
12

-continued
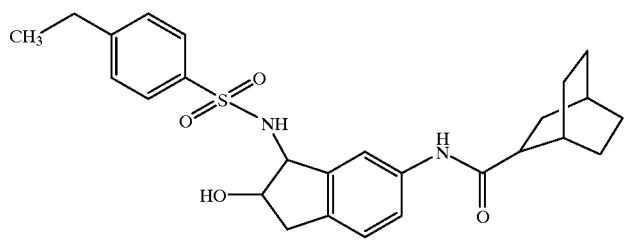
13
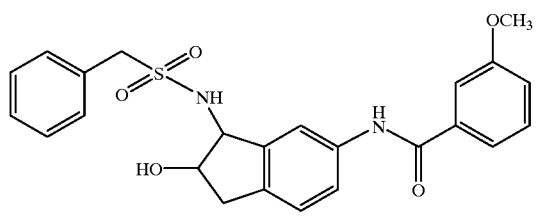
14
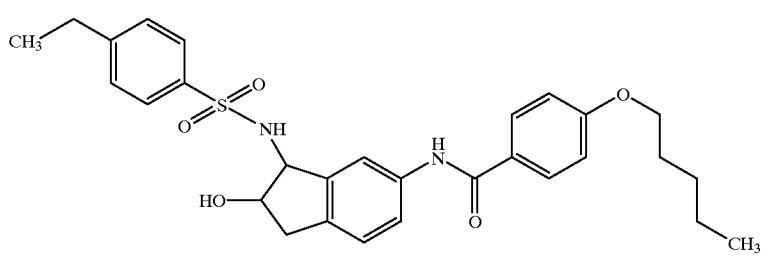
15
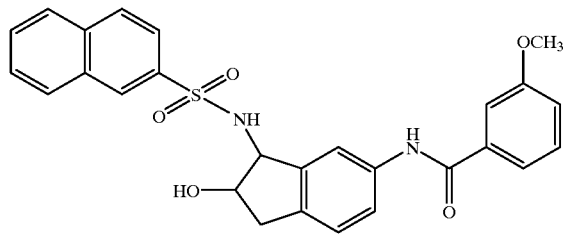
16
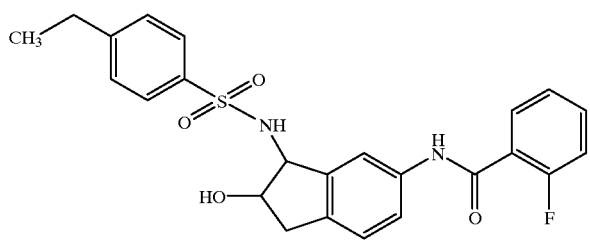
17
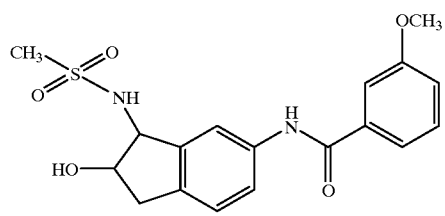
18

19
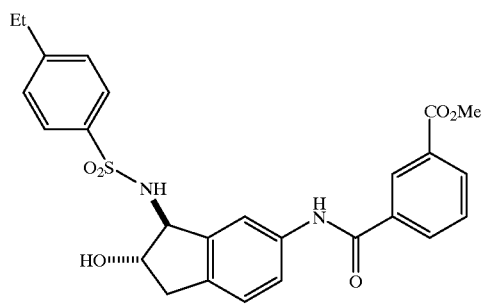
20
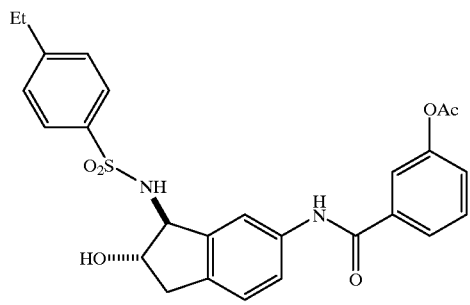
21
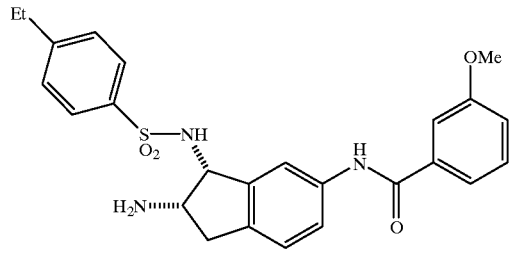
22
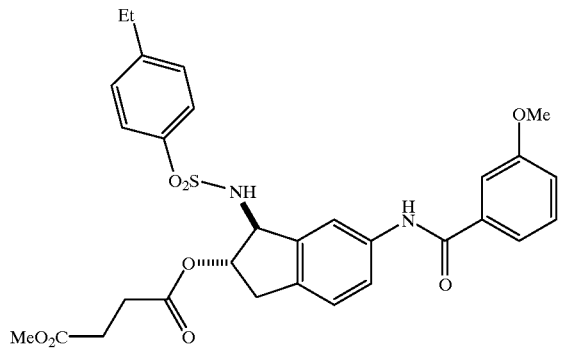
23
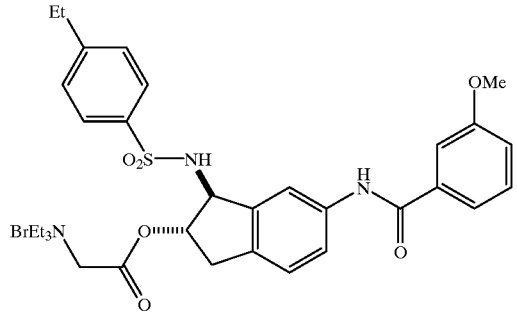

24
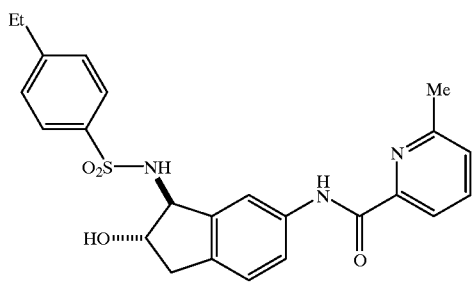
25
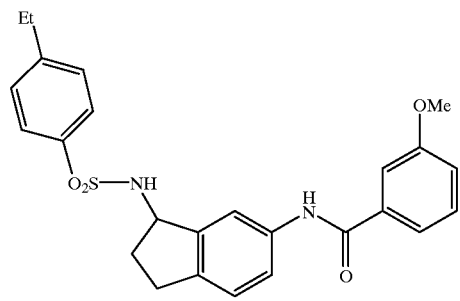
26
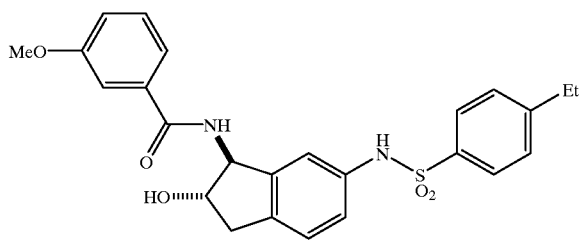
27
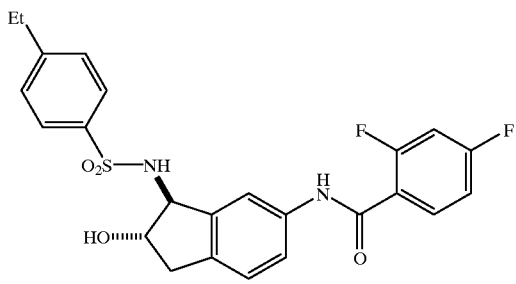
28
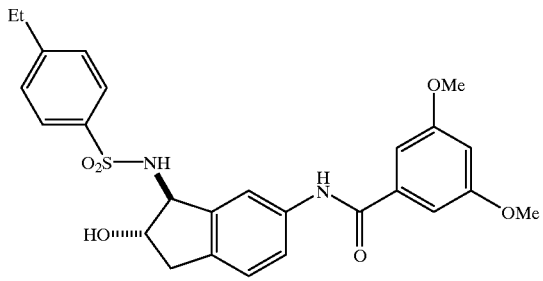
Examples of compounds described under Formula (III) include compounds 2, 4, 6, 8, 10, 11, 12, 13, 15, 16, 17, 19, 20, 24, 26, 27 and 28.
An interesting subgroup of Formula I compounds is illustrated in Formula IV (shown below).

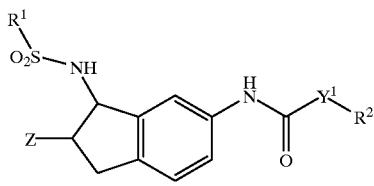

(IV)

wherein, the variables are as described for Formula I with the indicated preferences: $R^1$ is preferentially selected from the group of an optionally substituted aryl and an optionally substituted heteroaryl; $R^2$ is preferentially selected from the group of an optionally substituted aryl and an optionally substituted heteroaryl and Z is preferentially H or $OR^5$, with $R^5$ as defined above. $R^1$ and $^2$ are preferably moieties that are non-ionized at a physiological pH.

The term "alkyl" as used alone or in combination herein refers to a straight or branched chain saturated hydrocarbon group containing from one to ten carbon atoms and the terms "$C_{1-6}$ alkyl" and "lower alkyl" refer to such groups containing from one to six carbon atoms, such as methyl, ethyl, n-propyl, isopropyl, n-butyl, isobutyl, sec-butyl; tert-butyl and the like.

The term "alkoxy" as used alone or in combination herein refers to a straight or branched chain alkyl group covalently bonded to the parent molecule through an —O— linkage containing from one to ten carbon atoms and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The term "alkoxyalkyl" refers to an alkyl group substituted with an alkoxy group.

The term "haloalkyl" is a substituted alkyl, preferably a substituted lower alkyl, substituted with one or more halogen atoms, and preferably is a $C_1$ to $C_4$ alkyl substituted with one to three halogen atoms. One example of a haloalkyl is trifluoromethyl.

The term "alkanoyl" as used alone or in combination herein refers to an acyl radical derived from an alkanecarboxylic acid, particularly a lower alkanecarboxylic acid, and includes such examples as acetyl, propionyl, butyryl, valeryl, and 4-methylvaleryl.

The term "aminocarbonyl" means an amino-substituted carbonyl (carbamoyl or carboxamide) wherein the amino group can be a primary, secondary (mono-substituted amino) or tertiary amino (di-substituted amino) group preferably having as a substituent(s) a lower alkyl.

The term "carbocycloalkyl" refers to stable, saturated or partially unsaturated monocyclic, bridged monocyclic, bicyclic, and spiro ring hydrocarbyls of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. The term "optionally substituted" as it refers to "carbocycloalkyl" herein indicates that the carbocycloalkyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heterocyclyl" as used herein refers to a stable, saturated, or partially unsaturated, monocyclic, bridged monocyclic, bicyclic, and spiro ring system containing carbon atoms and other atoms selected from nitrogen, sulfur and/or oxygen. Preferably, a heterocyclyl is a 5 or 6-membered monocyclic ring or an 8–11 membered bicyclic ring which consists of carbon atoms and contains one, two, or three heteroatoms selected from nitrogen, oxygen and/or sulfur. The term "optionally substituted" as it refers to "heterocyclyl" herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower] alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclyl groups are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclyl group may be attached to the parent structure through a carbon atom or through any heteroatom of the heterocyclyl that results in a stable structure.

The term "heteroaryl" as used herein refers to a stable, aromatic monocyclic or bicyclic ring system containing carbon atoms and other atoms selected from nitrogen, sulfur and/or oxygen. Preferably, a heteroaryl is a 5 or 6-membered monocyclic ring (optionally benzofused) or an 8–11 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino, cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heteroaryl groups are isoxazolyl, imidazolyl, thiazolyl, isothiazolyl, pyridyl, furyl, pyrimidinyl, pyrazolyl, pyridazinyl, furazanyl and thienyl. The heteroaryl group may be attached to the parent structure through a carbon atom or through any heteroatom of the heteroaryl that results in a stable structure.

The specific chemical nature of the optionally substituted heterocyclyl and heteroaryl groups for the terminal moieties $R^1$ and $R^2$ in the prior identified potassium channel inhibitor compounds is not narrowly critical and, as noted above, a wide variety of substituent groups are contemplated. Preferably, the substituents for the heterocyclyl and heteroaryl groups are selected such that the total number of carbon and hetero atoms comprising the substituted heterocyclyls and heteroaryls is no more than about 20.

The terms "halo" and "halogen" as used herein to identify substituent moieties, represent fluorine, chlorine, bromine or iodine, preferably chlorine or fluorine.

The term "aryl" when used alone or in combination refers to an unsubstituted or optionally substituted monocyclic or bicyclic aromatic hydrocarbon ring system. Preferred are optionally substituted phenyl or naphthyl groups. The aryl group may optionally be substituted at one or more substitutable ring positions by one or more groups independently selected from alkyl (preferably lower alkyl), alkoxy (preferably lower alkoxy), nitro, monoalkylamino (preferably a lower alkylamino), diallylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Preferably, the aryl group is phenyl optionally substituted with up to four and usually with one or two groups, preferably selected from $C_{1-6}$ alkyl, $C_{1-6}$ alkoxy, as well as cyano, trifluoromethyl and halo.

The term "aralkyl" alone or in combination refers to an alkyl radical as defined above in which one hydrogen atom is replaced by an aryl radical as defined above, and includes benzyl, and 2-phenylethyl.

The term "alkoxycarbonyl" alone or in combination means a radical of the formula —C(O)-alkoxy, in which alkoxy is as defined above.

The term "alkylcarbonyloxy" alone or in combination means a radical of the formula —O—C(O)-alkyl, in which alkyl is as defined above.

The term "alkenyl" means a two to seven carbon, straight or branched hydrocarbon containing one or more double bonds, preferably one or two double bonds. Examples of alkenyl include ethenylene, propenylene, 1,3-butadienyl, and 1, 3, 5-hexatrienyl.

Unless otherwise defined, the term "optionally substituted" as used herein, refers to the substitution of a ring system at one or more positions with one or more groups selected from: $C_{1-6}$ alkyl, $C_{1-6}$ alkoxy, an optionally substituted phenyl, cyano, halo, trifluoromethyl, $C_{1-8}$ alkoxycarbonyl, $C_{1-6}$ alkyl carbonyloxy, mono- & bis-($C_{1-6}$ alkyl)-carboxamide, $C_{1-6}$ alkyl amido, nitro, and mono- & bis-($C_{1-6}$ alkyl)-amino.

The term "treating" as used herein, describes the management and care of a patient afflicted with a condition, disease or disorder for which the administration of a compound of the present invention alters the action or activity of a potassium channel to prevent the onset of symptoms or complications associated with the condition, disease or disorder, to alleviate the symptoms or complications caused by the condition, disease or disorder, or to eliminate the condition, disease or disorder altogether.

Indane compounds of the previous formulae useful as potassium channel inhibitors in accordance with the present invention can be prepared in accordance with the following sequential steps:

(1) Nitration of 1-indanone to yield a nitroindanone which is then separated from minor component byproducts;

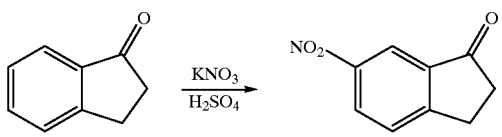

(2) Reduction of the product of step (1) to give the corresponding alcohol;

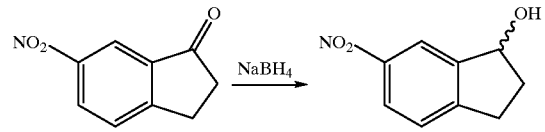

(3) Subjecting the product of step (2) to an acid catalyzed dehydration to give the corresponding indene;

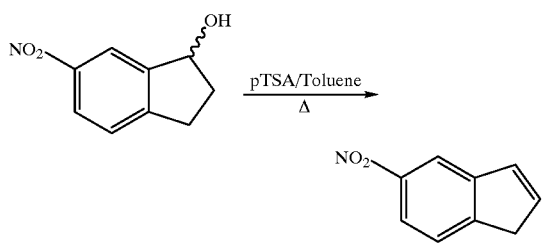

(4) Oxidizing the double bond of the product of step (3) to give the epoxide;

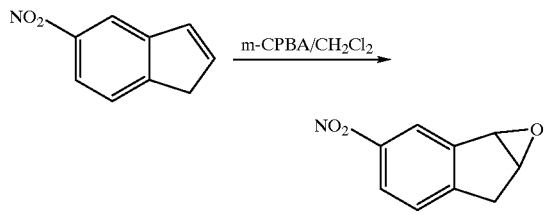

(5) Reacting the epoxide of step (4) with ammonium hydroxide to give the amino alcohol;

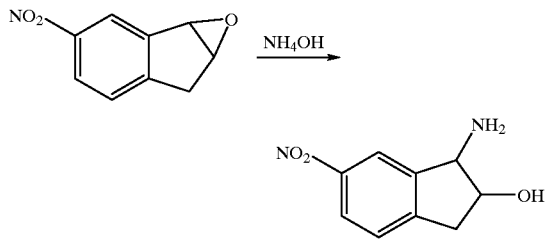

(6) Protecting the amino group of the amino alcohol with a conventional protecting group A wide variety of amino protecting groups are commonly employed to block or protect the —$NH_2$ functionality while reacting other functional groups on the parent compound. The species of protecting group used is not critical so long as the derivatized —$NH_2$ group is stable to the condition(s) of subsequent reaction(s) and can be removed at the appropriate point without disrupting the remainder of the molecule. See T. W. Greene and P. Wuts, *Protective Groups in Organic*

*Synthesis,* Chapter 7 (1991). Preferred amino-protecting groups are t-butoxycarbonyl (Boc), phthalimide, a cyclic alkyl, and benzyloxycarbonyl;

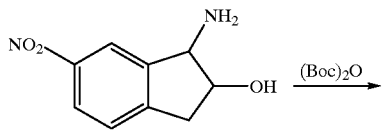

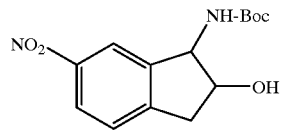

(7) Protecting the hydroxyl group of the amino alcohol with a conventional protecting group. A wide variety of hydroxy protecting groups are commonly employed to block or protect the —OH functionality while reacting other functional groups on the parent compound. The species of protecting group used is not critical so long as the derivatized —OH group is stable to the condition(s) of subsequent reaction(s) and can be removed at the appropriate point without disrupting the remainder of the molecule. See T. W. Greene and P. Wuts, *Protective Groups in Organic Synthesis,* Chapter 7 (1991). A suitable "hydroxy protecting group" includes one of the ether or ester derivatives of the hydroxy group commonly employed to block or protect the hydroxy group while reactions are carried out on other functional groups on a compound. Hydroxy protecting groups include tert-butyldiphenylsilyloxy (TBDPS), tert-butyldimethylsilyloxy (TBDMS), triphenylmethyl (trityl), mono- or di- methoxytrityl, or an alkyl or aryl ester;

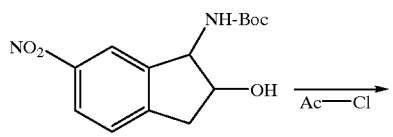

(8) Deprotecting the protected amino group of the product of step (7) resulting in an amino-functional indane;

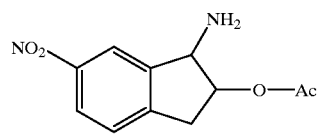

(9) Reacting the product of step (8) with a sulfonyl chloride to attach an R'—SO$_2$-moiety, where R' is equivalent to R$^1$ as defined in formula (I). The amino alcohol is reacted in a suitable solvent with the sulfonyl chloride (R'SO$_2$Cl) or sulfonyl anhydride in the presence of an acid scavenger. Suitable solvents in which the reaction can be conducted include methylene chloride and tetrahydrofuran. Suitable acid scavengers include triethylamine, and pyridine;

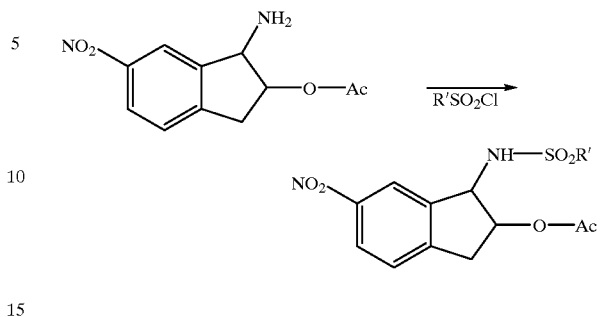

(10) Reducing the sulfonylated product of step (9) to give the corresponding aniline; and

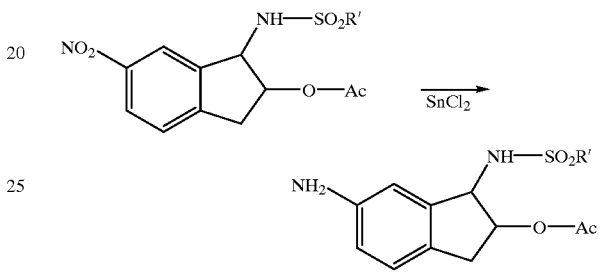

(11) Acylating the product of step (10) to attach the other substituent group, using RCOCl where R is equivalent to R$^2$ as defined in formula (I).

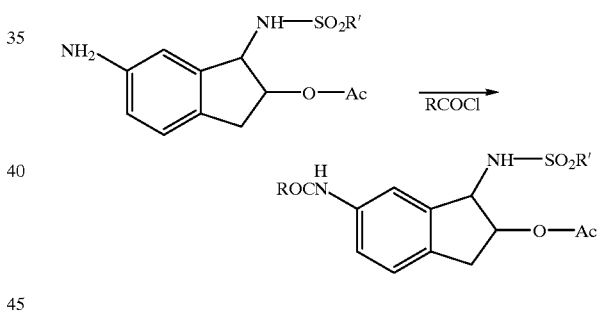

(12) Deprotecting the protected hydroxy group of the acylated product to produce the desired compound.

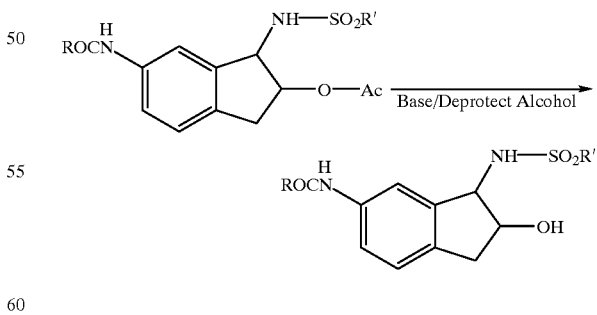

It is recognized that there are at least two chiral centers in the compounds falling within the scope of the present invention and thus such compounds will exist as various stereoisomeric forms. Applicants intend to include all the various stereoisomers within the scope of the invention. Thus, this invention is intended to include the cis and trans isomers and the corresponding enantiomers of the compounds of formula I–IV. Though the compounds may be prepared as racemates and can conveniently be used as such, individual enantiomers also can be isolated or preferentially synthesized by known techniques if desired. Such racemates and individual enantiomers and mixtures thereof are intended to be included within the scope of the present invention.

The present invention also encompasses the pharmaceutically acceptable prodrugs of the compounds of Formula I. A prodrug is a drug which has been chemically modified and may be biologically inactive at its site of action, but which is degraded or modified by one or more enzymatic or other in vivo processes to the parent bioactive form. Generally, a prodrug has a different pharmakokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, *Design of Prodrugs,* (1985). Those skilled in the art are well-versed in the preparation of prodrugs and are well-aware of its meaning.

The compounds of the present invention can be used in their neat form or in the form of pharmaceutically-acceptable salts derived from inorganic or organic acids. Examples of acids which may be employed to form pharmaceutically acceptable acid addition salts of compounds of the present invention include such inorganic acids as hydrochloric acid, sulphuric acid and phosphoric acid and such organic acids as oxalic acid, maleic acid, succinic acid and citric acid. These salts thus include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Also, the basic nitrogen-containing groups can be quaternized with such agents as lower alkyl halides, such as methyl, ethyl, propyl, and butyl chlorides, bromides and iodides; dialkyl sulfates, like dimethyl, diethyl, dibutyl and diamyl sulfates, long chain halides such as decyl, lauryl, myristyl and stearyl chlorides, omides and iodides, aralkyl halides like benzyl and phenethyl bromides and others. Water or oil soluble or dispersible products are thereby generally obtained.

The pharmaceutically acceptable salts of the compounds of the present invention also can exist as various solvates, such as with water, methanol, ethanol, dimethylformamide, ethyl acetate and the like. Mixtures of such solvates also can be prepared. Such solvates are within the scope of the present invention.

The pharmacological profile of the potassium channel inhibitory activity of the compounds of the present invention can be readily assessed by those skilled in the art using routine experimentation, such as the procedures and techniques illustrated in the examples which follow. Assays for assessing the activity of particular compounds may employ cells stably transfected to express a specific potassium channel, as well as native mammalian cells. In particular, cells stably transfected to express a specific potassium channel, which have been treated with a voltage dependent fluorescent dye, such as bis-(1,3-dibutylbarbituric acid) trimethine oxonol, can be used to gauge the inhibitory activity of potassium channel inhibitor compounds, possibly in comparison to known inhibitors. Alternatively, such cells can be primed with a detectible species, such as $^{86}Rb$, and then challenged with a particular compound, under conditions otherwise suitable for activating the potassium channel, to assess the potassium inhibitory activity of the compound. The potassium channel inhibitory activity of a compound also can be determined using isolated mammalian cells and the whole cell configuration of the known patch clamp technique (Hamill et al., *Pflugers Archiv* 391:85, 1981). These and other known techniques can be readily employed by those skilled in the art to assess the activity level of the potassium channel inhibitor compounds of the present invention.

The compounds of the present invention may be administered by a variety of routes including orally, parenterally, sublingually, intranasally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intracardiac injection, or infusion techniques. Topical administration may also involve the use of transdermal administration such as transdermal patches or iontophoresis devices.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,2-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The compounds of the present invention can also be administered in the form of liposomes. As is known in the art, liposomes are generally derived from phospholipids or other lipid substances. Liposomes are formed as mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York N.Y. (1976), p. 33, et seq.

To select preferred compounds from less preferred compounds, one uses by example the in vitro assays detailed under the sub-heading BioAssays hereafter. Typically, a preferred compound will produce half maximal blocking activity at a concentration ranging from about 10 nM to about 1 $\mu$M in the in vitro assays described. One of ordinary skill will recognize that the final and optimum dose and regimen will be determined empirically for any given drug.

Total daily dose administered to a host in single or divided doses may be an amount, for example, from 0.001 to 100 mg of active ingredient per kg body weight on a daily basis and more usually 0.01 to 10 mg/kg/day. Dosage unit compositions may contain such amounts of submultiples thereof to make up the daily dose. It is anticipated that a therapeutically effective serum concentration of active ingredient will be 10 nM to 10 $\mu$M (5 ng/ml to 5 $\mu$g/ml).

The amount of active ingredient that may be combined with carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, and diet of the patient, the time of administration, the route of administration, the rate of excretion, whether a drug combination is used, and the severity of the particular disease.

The present invention is explained in greater detail in the Examples which follow. These examples are intended as illustrative of the invention, and are not to be taken as limiting thereof. Unless otherwise indicated, all references to parts and percentages are based on weight and all temperatures are expressed in degrees Celsius. The scope of the invention is not construed as merely consisting of the following examples.

EXAMPLES

Compound Preparation

Preparation 1

1. To a solution of 1-indanone (25 g. 0.189 mol) in concentrated $H_2SO_4$ (84 ml) at 0° C. was added a solution of $KNO_3$ (8.33 g. 0.0824 mol) in $H_2SO_4$ (40 ml) so as to maintain an internal temperature below 15° C. After stirring at 0° C. for 1 hr., the reaction mixture was poured into crushed ice and stirred vigorously for 30 min. The suspension was then filtered, air dried, and purified by LC 95% ethyl acetate/toluene) to provide the nitrated indanone (18.90 g, 56%) as a pale yellow solid.

2. A solution of the nitrated product (18.90 g. 0.107 mol) in methanol (300 ml) was cooled to 0° C. and $NaBH_4$ (4.04 g. 0.107 mol) was added in several small portions. The reaction was then stirred overnight at 25° C. The solution was quenched at 0° C. with methanolic HCl (200 ml), concentrated under reduced pressure, redissolved in $CH_2Cl_2$, washed with $H_2O$, and the organic layer reconcentrated to provide the crude alcohol as a brown solid.

3. To a solution of crude alcohol in toluene (300 ml) was added a catalytic amount of p-toluenesulfonic acid and the reaction was heated at reflux for 1 hr. using a Dean Stark trap to remove the $H_2O$. The organic layer was washed with saturated aqueous $NaHCO_3$ (3×200 ml), dried over $MgSO_4$, solvent removed under vacuum, and the product recrystallized from methanol to afford the corresponding indene (13.41 g, 78% over two steps) as a tan solid.

4. To a solution of the indene (10.53 g, 0.0653 mol) in dichloromethane (350 ml) at 0° C. was added m-CPBA 929 g. 0.0924 mol) in small amounts over the course of 1 hr. After stirring overnight at 25° C., the mixture was washed with saturated aqueous $Na_2SO_3$ (2×200 ml), saturated aqueous $NaHCO_3$ (2×200 ml), filtered through a cotton plug, and concentrated under vacuum.

5. A suspension of the resulting epoxide in concentrated $NH_4OH$ (250 ml) was heated overnight in an oil bath at 45° C. The next day $H_2O$ was added and the basic aqueous layer was saturated with NaCl. The cloudy reaction mixture was extracted with THF until no more product could be seen by TLC. Organic layers were combined, dried over $MgSO_4$, concentrated, and recrystallized from ethyl acetate to give the corresponding amino alcohol (11.54 g, 91% over two steps) as a fluffy tan solid.

6. To a solution of the amino alcohol (8.34 g, 0.0429 mol) in THF (200 ml) was added a solution of di-tert-butyldicarbonate (11.25 g, 0.0515 mol) in THF (50 ml). After stirring 1 hr. at 25° C., the solvent was removed under reduced pressure and the resulting solid was recrystallized from ethyl acetate to afford the corresponding amino-protected compound (11.34 g, 90%) as a white solid.

7. Under $N_2$ atmosphere a 3 L three-necked round bottomed flask equipped with an overhead stirrer and addition funnel was charged with carboxylated polystyrene resin (70 g, 2.77 nmol $CO_2H$/g resin), anhydrous dichloromethane (1000 ml), and anhydrous DMF (10 ml). Next, oxalyl chloride (60.75 ml, 0.582 mol) was added via a slow dropwise addition from an addition funnel. After heating at reflux overnight under $N_2$, the solvent was removed under vacuum using a gas dispersion tube. The resin was subsequently washed with anhydrous dichloromethane (3×500 ml). Once the last wash was complete, the resin was dried under vacuum for 2–3 hrs. At this time, the polymer was resuspended in dry THF (1000 ml) followed by the addition of dry pyridine (314 ml, 3.88 mol), DMAP (11.85 g, 0.0970 mol), and the amino-protected compound (85.62 g, 0.291 mol). The mixture was heated at reflux for 10 days under an inert atmosphere. The solvent was removed by vacuum filtration and the resin was washed with THF (3×300 ml), $CH_2Cl_2$ (3×300 ml), and dried overnight in a vacuum oven to provide a resin bonded amino protected indane (122.18 g) as a tan resin.

8. Into a round bottomed flask equipped with a stir bar was placed the resin bonded indane (28 mg, 0.02827 mol), 0.500 ml dichloromethane, and TFA (0.109 ml, 0.14135 nmol).

The reaction mixture was stirred at 25° C. overnight, resin collected by filtration, resuspended in 10% TEA/CH$_2$Cl$_2$, stirred for 15 min., filtered again, and finally washed with dichloromethane to afford the amino deprotected species.

9. Into a 10 ml round bottomed flask was placed the resin bonded, amino deprotected species (0.02827 mmol) followed by 0.5 ml of a solution of pyridine (0.03659 ml, 0.4524 mmol) and DMAP (0.518 mg, 0.004241 mmol) in dichloromethane. Next, a 1 M solution of an electrophile (e.g., an aroyl chloride) in dichloromethane (0.1838 ml, 0.1838 mmol) was added and the resulting mixture was stirred overnight at 25° C. At this time the solvent was removed by vacuum filtration and the resin was washed with CH$_2$Cl$_2$, DMF, methanol, DMF, methanol, and CH$_2$Cl$_2$.

10. To a solution of the corresponding acylated compound (0.02827 mmol) in DMF (0.625 ml) was added SnCl$_2$×2 H$_2$O (102 mg, 0.4524 mmol) to convert the nitro group into an amino group. Upon stirring at 25° C. for 48 hrs, the resin was isolated by filtration and washed with CH$_2$Cl$_2$, DMF, methanol, DMF, methanol, and CH$_2$Cl$_2$.

11. Into a 10 ml round bottomed flask was placed the amino functional compound (0.02827 mmol) followed by 0.5 ml of a solution of pyridine (0.03659 mmol) and DMAP (0.518 mg, 0.004241 mmol) in dichloromethane. Next, a 1 M solution of an electrophile (e.g., a sulfonyl chloride) in dichloromethane (0.1838 ml, 0.1838 mmol) was added and the resulting mixture was stirred overnight at 25° C. At this time the solvent was removed by vacuum filtration and the resin was washed with CH$_2$Cl$_2$.

12. To a flask containing the compound of step 11 (0.02827 mmol) was added a 1 M solution of NaOH in methanol (0.375 ml, 0.375 mmol) and THF (0.400 ml). After overnight stirring at 25° C., the reaction was neutralized with 4 M HCL in methanol (0.100 ml, 0.400 mmol), resin filtered, and the filtrate was concentrated under reduced pressure to provide the desired target compound.

Preparation 2 trans-1-benzamido-2-acetoxy-6-aminoindane

One part trans-1-tert-butyloxycarbamido-2-hydroxy-6-nitroindane is dissolved in a mixture of pyridine (16 parts), 4-dimethylaminopyridine (0.15 parts) and THF as acetyl chloride (1.2 parts) is added dropwise. After several hours, the reaction is treated with cold water and the organic layer separated. The organic solution is washed with cold 1 N HCL, the organic layer dried, and the solvent evaporated to give trans-1-tert-butyloxycarbamido-2-acetoxy-6-nitroindane. A solution of this amino- and hydroxy-protected nitroindane in THF is treated with a stream of dry HCl for 5 minutes then stirred for an additional hour. The solution is carefully treated with cold saturated sodium bicarbonate, the organic phase is washed with water, dried and the solvent evaporated to give trans-1-amino-2-acetoxy-6-nitroindane. A solution of amino deprotected compound in a mixture of pyridine (16 parts), 4-dimethylaminopyridine (0.15 parts), and CH$_2$Cl$_2$ is treated with a solution of a benzoyl chloride (1.2 parts) and the reaction stirred over night. The reaction is poured into ice-water, the organic layer separated and consecutively washed with 1 N HCl and brine. The organics are dried and the solvent evaporated to give trans-1-benzamido-2-acetoxy-6-nitroindane. A solution of this acylated product (one part) in DMF is treated with SnCl$_2$.2 H$_2$O (16 parts) and stirred over night. The reaction is poured into ice-water, the reaction made basic, and the mixture extracted with CH$_2$Cl$_2$. The organic extracts are washed with brine, the solution dried, and the solvent evaporated to give trans-1-benzamido-2-acetoxy-6-aminoindane.

Preparation 3 trans-1-benzamido-2-hydroxy-6-carboxamido-indane

A solution of trans-1-benzamido-2-acetoxy-6-nitroindane (one part), prepared as described in Preparation 2, in EtOAc is treated with H$_2$ (60 psi) in the presence of PtO$_2$ for several hours. The catalyst is removed and the solvent evaporated to give trans-1-benzamido-2-acetoxy-6-aminoindane. A solution of this aminoindane (1 part) in a mixture of pyridine (16 parts), 4-dimethylaminopyridine (0.15 parts), and CH$_2$Cl$_2$ is treated with a solution of an aroyl (RCOCl) chloride (1.2 parts) and the reaction stirred over night. The reaction is poured into ice-water, the organic layer separated and consecutively washed with saturated aqueous sodium bicarbonate and brine. The organics are dried and the solvent evaporated to give trans-1-benzamido-2-acetoxy-6-carboxamino-indane. A solution of this indane in 1 M NaOH in methanol was stirred over night. The reaction is poured into ice-water and extracted with CH$_2$Cl$_2$. The organic extracts are washed with brine, dried, and the solvent evaporated to give the trans-1-benzamido-2-hydroxy-6-carboxamnido-indane.

Preparation 4 trans- 1-benzamido-2-hydroxy-6-carboxamido-indane

A solution of a benzamide (2 parts) in DMF is treated with NaH (2 parts) and the reaction is stirred until gas evolution ceases. To the reaction is added 1,2-epoxy-6-nitroindane (1 part) and the reaction is stirred over night at 60° C. The reaction is poured into ice-water and extracted with CH$_2$Cl$_2$. The organic extracts are washed with water, dried, and the solvent evaporated. The residue is chromatographed to obtain trans-1-benzamido-2-hydroxy-6-nitroindane. To a solution of the nitroindane (1 part) in a mixture of pyridine (16 parts), 4-dimethylaminopyridine (0.15 parts) and an inert organic solvent such as THF or CH$_2$Cl$_2$, acetyl chloride (1.2 parts) is added dropwise. After several hours, the reaction is treated with cold water and the organic layer separated. The organic solution is washed with cold 1 N HCL, the organic layer dried, and the solvent is evaporated to give trans-1-benzamidoamido-2-acetoxy-6-nitroindane. Processing of this protected indane as in Preparation 2 provides the trans-1-benzamido-2-hydroxy-6-carboxamido-indane.

Preparation 5

1-benzamido-6-carboxamidoindane

A mixture of 6-nitroindan-1-one (1 part) and Raney-Ni in EtOH is treated with hydrogen (60 psi) for several hours. The catalyst is removed and the solvent evaporated to give 6-aminoindan-1-one. A solution of the aminoindanone (1 part) in a mixture of pyridine (16 parts), 4-dimethylaminopyridine (0.15 parts), and CH$_2$Cl$_2$ is treated with a solution of an acyl chloride (1.2 parts) and the reaction is stirred overnight. The reaction is poured into ice-water, the organic layer separated and consecutively washed with saturated aqueous sodium bicarbonate and brine. The organics are dried and the solvent evaporated to give the 6-carboxamido-indan-1-one. A solution of this product (1 part) in a mixture of EtOH and $NH_3$ (5 parts) is treated with hydrogen (60 psi) in the presence of Pd—C-sulfided. After several hours, the catalyst is removed and the solvent evaporated to give 1-amino-6-carboxamido-indane. A solution of the indane (1 part) in a mixture of pyridine (16 parts), 4-dimethylaminopyridine (0.15 parts), and $CH_2Cl_2$ is treated with a solution of a benzoyl chloride (1.2 parts) and the reaction stirred over night. The reaction is poured into ice-water, the organic layer separated and consecutively washed with saturated aqueous sodium bicarbonate and brine. The organics are dried and the solvent evaporated to give the 1-benzamido-6-carboxamido-indane.

The column chromatography procedures used standard flash chromatography techniques. One well-known reference describing appropriate flash chromatography techniques is Still, W. C. Kahn, and Nitra, *J. Org. Chem.* 43:2932 (1978). Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate and treating with maleic acid. The precipitate formed was filtered and dried to provide the corresponding maleate salt of the free base.

Preparation 6

Synthesis of Compound 4

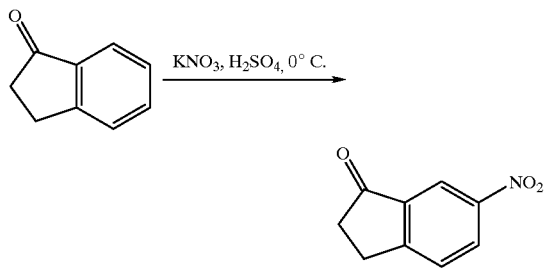

To ice cold conc. $H_2SO_4$ (100 mL) was added 1-indanone (15 g, 0.11 mol) followed by slow addition (2 h) of $KNO_3$ (17 g, 1.5 eq) as a solution in conc. $H_2SO_4$ (50 mL). The resulting mixture was poured onto packed granular ice (1.5 L) and diluted with water (total aqueous layer was 1 L) and $Et_2O$ (1 L). The $Et_2O$ layer was separated and washed with water (2×200 mL). The combined aqueous layers was slowly treated with KOH (75 g) and extracted with $CH_2Cl_2$ (2×500 mL). The combined $CH_2Cl_2$ layers was washed with water (500 mL). The combined organic layers was dried ($Na_2SO_4$), filtered, and treated with silica gel (30 g). The resulting solid was applied to a column of silica gel (2.5"× 13") and purified by flash chromatography. Removal of the solvent provided the product as a solid (14.5 g, 74%). $R_f$ (silica gel): 0.23 (30% EtOAc, 70% hexanes). $^1$H NMR (300 MHZ, $CDCl_3$) δ 8.42 (s, 1H), 8.37 (dd, J=2.1, 8.4, 1H), 7.65 (d, J=8.3, 1H), 3.26 (m, 2H), 2.78 (m, 2H). $^{13}$C NMR (75 MHZ, $CDCl_3$) δ 204.71, 160.94, 147.76, 138.04, 128.73, 127.88, 118.90, 36.49, 25.98.

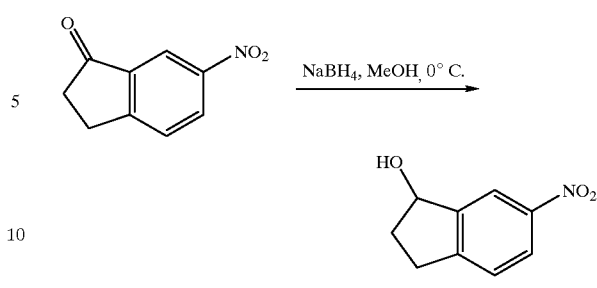

The 6-nitro-1-indanone (14.5 g, 0.082 mol) was dissolved in MeOH (160 mL) and cooled to 0° C. The $NaBH_4$ (3.2 g, 1 eq, granular) was added in 5 portions with 20 min intervals. The resulting mixture was allowed to stir for 12 h, slowly coming to rt. The mixture was then cooled to 0° C. again, treated dropwise with 6 N HCl (40 mL, 3 eq) and diluted with water (800 mL) and $CH_2Cl_2$ (400 mL). The aqueous layer was separated and extracted with $CH_2Cl_2$ (2×100 mL). The combined organic layers was dried ($Na_2SO_4$) and filtered. Removal of the solvent provided the product as a solid (14.6 g, 99%) which was used in the next step without further purification. $R_f$ (silica gel): 0.15 (5% EtOAc, 45% hexanes, 50% $CH_2Cl_2$).

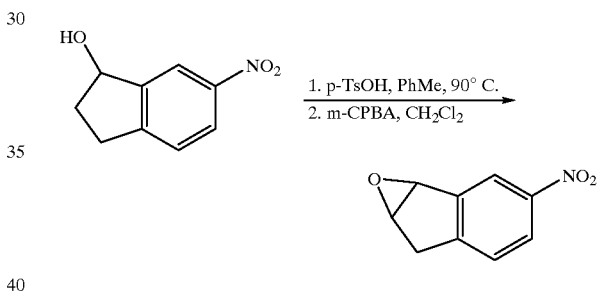

The 1-hydroxy-6-nitroindane (14.6 g, 0.082 mol) was heated with p-TsOHH$_2$O (1.5 g, 0.1 eq) in PhMe (80 mL) for 3 h at 90° C. Most of the solvent was removed and the resulting mixture diluted with CH2Cl$_2$ (240 mL). The m-CPBA (34 g, 1.2 eq) was added in four portions with 20 min intervals. The mixture was left to stir for 12 h, treated with sat. aqueous $NaHCO_3$ (400 mL), stirred for an additional 30 min, and then diluted with $H_2O$ (200 mL) and $CH_2Cl_2$ (100 mL). The aqueous layer was separated and extracted with $CH_2Cl_2$ (2×100 mL). The combined organic layers was dried ($Na_2SO_4$) and filtered (2" of silica gel). Removal of the solvent provided the product as a solid (14 g, 96%) which was used in the next step without further purification. $R_f$ (silica gel): 0.49 (5% EtOAc, 45% hexanes, 50% $CH_2Cl_2$). $^1$H NMR (300 MHZ, $CDCl_3$) δ 8.34 (s, 1H), 8.16 (d, J=8.2, 1H), 7.38 (d, J=8.2, 1H), 4.35 (d, J=1.9, 1H), 4.22 (d, J=2.7, 1H), 3.31 (d, J=18.9, 1H), 3.06 (dd, J=2.5, 18.8, 1H).

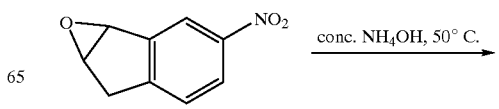

-continued

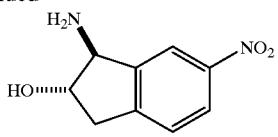

The 6-nitro-1,2-epoxyindane (3.0 g, 17 mmol) was suspended in concentrated NH$_4$OH (60 mL) and stirred for 12 h at 35° C. and for 4 h at 50° C. The resulting dark mixture was diluted with brine (170 mL), saturated with NaCl, subjected to mild vacuum, and stirred with 15% I-PrOH/CHCl$_3$ (170 mL). The aqueous layer was separated and extracted with 15% I-PrOH/CHCl$_3$ (4×50 mL). The combined organic layers was dried (Na$_2$SO$_4$) and filtered. Removal of the solvent provided the product as a tan solid (3.0 g, 91%) which was used in the next step without further purification. R$_f$ (silica gel): 0.20 (2% AcOH, 18% MeOH, 80% CHCl$_3$).

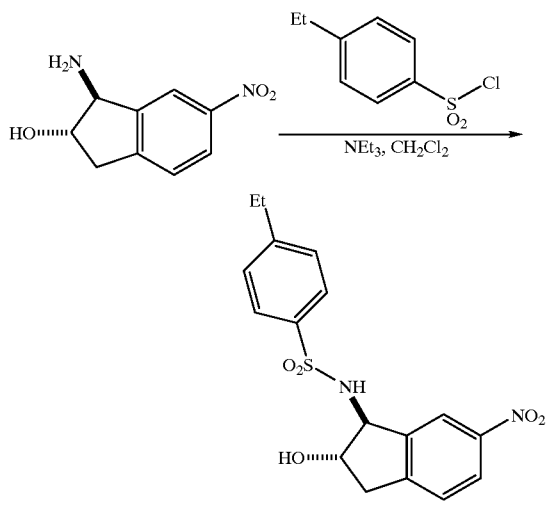

To an ice cold suspension of the aminoindane derivative (390 mg, 2.0 mmol) in dry CH$_2$Cl$_2$ (6 mL), was added NEt$_3$ (0.33 mL, 1.2 eq) followed by slow addition of the sulfonyl chloride (451 mg, 1.1 eq) as a solution in CHCl$_2$ (2 mL). The ice bath was removed and the heterogeneous mixture was left to stir for 3 h. The resulting homogeneous mixture was diluted with CH$_2$Cl$_2$ (8 mL), water (8 mL), and sat. aqueous NH$_4$Cl (2 mL). The organic layer, along with the precipitated product, was separated from the aqueous layer. The aqueous layer was extracted with CH$_2$Cl$_2$ (3×2 mL). The combined organic layers was treated with I-PrOH (3 mL), dried (Na$_2$SO$_4$), and filtered. Most of the solvent was removed and to the resulting solid was added hexanes/CH$_2$Cl$_2$ (1/1, 20 mL). The solid was filtered, washed with hexanes/CH$_2$Cl$_2$ (1/1, 10 mL), and subjected to high vacuum to provide the product (600 mg, 83%). R$_f$ (silica gel): 0.27 (30% EtOAc, 20% hexanes, 50% CH$_2$Cl$_2$). $^1$H NMR (300 MHZ, CDCl$_3$) δ 7.97 (d, J=8.3, 1H), 7.81 (d, J=8.2, 2H), 7.33 (d, J=7.9, 2H), 7.21–7.26 (m, 2H), 4.49 (d, J=6.1, 1H), 4.36 (dd, J=7.2, 13.8, 1H), 3.30 (bs, 2H), 3.21 (dd, J=7.1, 16.7, 1H), 2.78 (dd, J=7.4, 16.8, 1H), 2.69 (q, J=7.7, 2H), 1.21 (t, J=7.5, 3H). $^{13}$C NMR (75 MHZ, CDCl$_3$) δ 150.35, 147.44, 147.35, 141.41, 137.57, 128.84, 126.96, 125.60, 123.87, 119.57, 79.33, 64.55, 37.66, 28.53, 14.62.

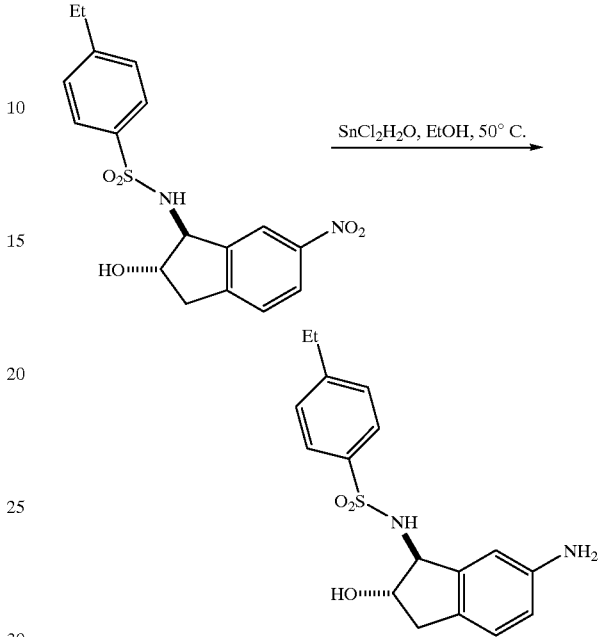

To a suspension of the nitroindane derivative (5.2 g, 14 mmol) in absolute EtOH (70 mL) was added SnCl$_2$.2H$_2$O (13 g, 14 eq). After heating the mixture at 50° C. for 12 h, most of the EtOH was removed and the resulting residue treated with CHCl$_3$ (70 mL), sat. aqueous NaHCO$_3$ (140 mL), and water (70 mL). The mixture was stirred for 30 min and then diluted with 15% I-PrOH/CHCl$_3$ (70 mL) and water (70 mL). The aqueous layer (containing precipitated tin byproduct) was extracted with 15% I-PrOH/CHCl$_3$ (3×70 mL). The combined organic layers was dried (Na$_2$SO$_4$) and filtered. Removal of the solvent provided the product as a solid (4.5 g, 97%) which was used in the next step without further purification. R$_f$ (silica gel): 0.23 (30% EtOAc, 20% hexanes, 50% CH$_2$Cl$_2$.

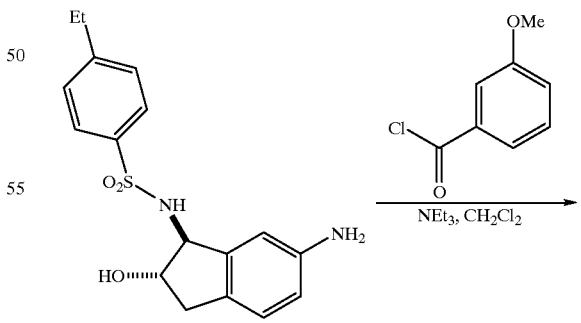

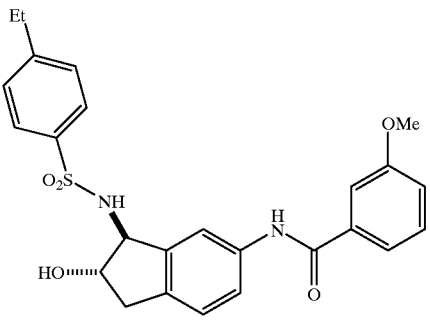

Compound 4

To an ice cold suspension of the 6-aminoindane derivative (2.3 g, 6.9 mmol) in dry CH$_2$Cl$_2$ (21 mL) was added the acid chloride (1.2 g, 1.05 eq) followed by slow addition of the NEt$_3$ (1.2 mL, 1.2 eq). The ice bath was removed and after 1 h, the resulting homogeneous mixture was treated with CH$_2$Cl$_2$ (20 mL), water (35 mL), and sat. aqueous NH$_4$Cl (7 mL). The aqueous layer was separated and extracted with CH$_2$Cl$_2$ (3×20 mL). The combined CH$_2$Cl$_2$ layers was dried (Na$_2$SO$_4$), filtered & treated with silica gel (7 g). Evaporation of the solvent provided a solid which was applied to a column of silica gel (1.5"×9") and purified by flash chromatography. Removal of the solvent provided the product as a crystalline solid (3.0 g, 93%). R$_f$ (silica gel): 0.16(30% EtOAc, 20% Hexanes, 50% CH$_2$Cl$_2$). $^1$H NMR (300MHZ, DMSO-d6) δ 10.16 (s, 1H), 8.09 (d, J=8.3, 1H), 7.80 (d, J=8.4, 2H), 7.37–7.59 (m, 7H), 7.10–7.15 (m, 2H), 5.03 (d, J=5.6, 1H), 4.40–4.45 (m, 1H), 4.03–4.09 (m, 1H), 3.83 (s, 3H), 3.02 (dd, J=6.8, 15.8, 1H), 2.64 (q, J=7.5, 2H), 2.50–2.57 (m, 1H), 1.16 (t, J=7.7, 3H). HRMS (FAB) m/e calcd. for C$_{25}$H$_{27}$N$_2$O$_5$S (MH$^+$) 467.1640, obsd. 467.1648.

Separation of the enantiomers of compound 4 was performed by HPLC with a Chiralpak AS column (Chiral Technologies), eluting with hexanes/ethanol/methanol (60/20/20). Analytical separation of the enantiomers with a 4.6 mm×250 mm column and a flow rate 1 mL/min resulted in retention times 6.7 (1R, 2R) and 11.1 (1S, 2S) minutes.

Alternatively, compound 4 could be prepared enantioselectively via the asymmetric epoxidation described below.

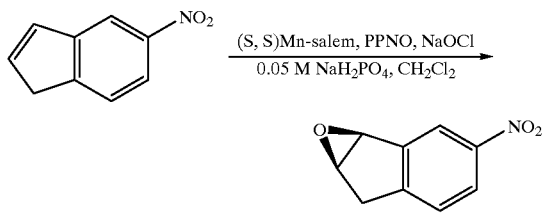

To a solution of 5-nitroindene (1.28 g, 7.94 mmol) in CHCl$_2$ (5 mL) was added 415 mg (2.42 mmol) of 4-phenylpyridine-N-oxide followed by 154 mg (0.24 mmol) of (S,S)-N,N'-bis-(3,5-di-tert-butylsalycidene)-1,2-cyclohexanediaminomanganese (III) chloride. After cooling to 0° C., 12 mL of 0.05 M NaH$_2$PO$_4$ was added followed by ice cold 10–13% NaOCl. After 1 h at 0° C., the reaction mixture was filtered (celite), washing with CH$_2$Cl$_2$ (200 mL). The aqueous layer was separated and extracted with CH$_2$Cl$_2$ (50 mL). The combined organic phase was washed with H$_2$O (50 mL) and brine (50 mL) and then dried over Na$_2$SO$_4$. Purification by flash chromatography using silica gel (1:1; hexanes:Et$_2$O) gave the (1S, 2R)-epoxide (988 mg, 71%, 70% ee) as a yellow solid.

The enantiomeric excess was determined by HPLC with a Chiralcel OB-H column (Chiral Technologies), eluting with hexanes/isopropyl alcohol (80/20; 1 mL/min). With a 4.6 mm×250 mm column the retention times of the enantiomers are 33.6 and 36.3 minutes. This enantioenriched epoxide was then used to prepare enantioenriched compound 4, as described above. Further enantioenrichment (>90% ee) was obtained by recrystallization of compound 4 from I-PrOH-hexanes.

Preparation 7

Synthesis of Compound 24

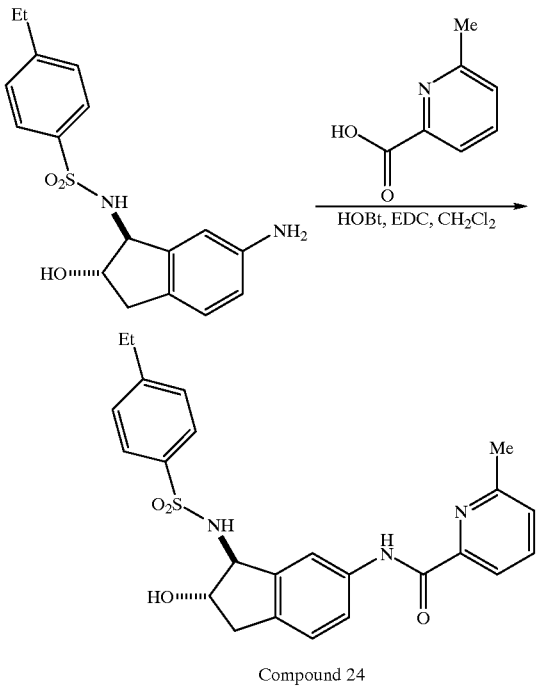

Compound 24

To a heterogeneous mixture of the carboxylc acid (36 mg, 1.1 eq) and CH$_2$Cl$_2$ (2.5 mL), was added HOBt (39 mg, 1.2 eq) followed by EDC (60 mg, 1.3 eq). After 20 min a homogeneous mixture resulted, which was treated with the 6-aminoindane derivative (80 mg, 0.24 mmol). After stirring for 6 h, the mixture was diluted with CHCl$_3$ (2 mL), brine (2 mL), and sat. aqueous NaHCO$_3$ (2 mL). The aqueous layer was separated and extracted with CHCl$_3$ (3×2 mL). The combined organic layers was dried (Na$_2$SO$_4$), filtered, and treated with silica gel (300 mg). Removal of the solvent provided a solid which was applied to a column of silica gel (0.5"×7") and purified by flash chromatography. Removal of the solvent provided the product as a solid (108 mg, 100%). R$_f$ (silica gel): 0.45 (50% EtOAc, 50% CH$_2$Cl$_2$). $^1$H NMR (300 MHZ, CDCl$_3$) δ 9.95 (s, 1H), 7.98 (d, J=7.7, 1H), 7.87 (d, J=8.2, 2H), 7.73 (dd, J=7.6, 7.6, 1H), 7.37 (d, J=8.1, 1H), 7.20–7.35 (m, 4H), 7.08 (d, J=8.1, 1H), 6.93 (d, J=5.6, 1H), 4.30–4.50 (m, 2H), 3.13 (dd, J=6.7, 15.4, 1H), 2.50–2.80 (m, 6H), 1.14 (t, J=7.6, 3H). $^{13}$C NMR (75 MHZ, CDCl$_3$) δ 162.53, 157.36, 149.69, 148.57, 139.70, 137.84, 137.28, 136.29, 135.68, 128.62, 127.32, 126.42, 125.38, 120.86, 119.47, 116.14, 80.41, 65.17, 37.06, 28.50, 23.94, 14.72.

Preparation 8
Synthesis of Compound 22

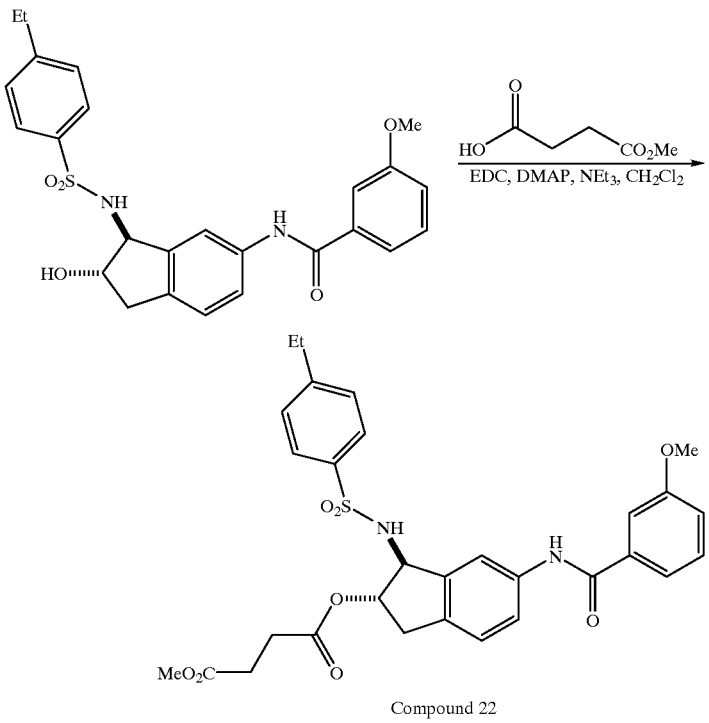

Compound 22

A suspension of the 6-amidoindane derivative (0.174 g, 0.373 mmol) in dry $CH_2Cl_2$ (10 ml) was treated with EDC-HCl (0.120 g, 0.626 mmol), 4-DMAP (0.100 g, 0.819 mmol), $NEt_3$ (0.080 ml, 0.57 mmol) and mono-methyl succinate (0.079 g, 0.60 mmol). The resulting homogeneous reaction mixture was stirred at room temperature for 2.5 h and treated with $H_2O$ (15 ml), saturated aqueous $NH_4Cl$ (15 ml) and $CHCl_2$ (20 ml). The organic layer was separated, washed with brine, dried ($Na_2SO_4$), filtered and concentrated. Flash chromatography on silica provided the product as a white solid (0.190g, 88%). $R_f$ (silica gel): 0.75 (20% hexanes: 20% $CH_2Cl_2$: 60% EtOAc). $^1H$ NMR (300 MHZ, DMSO-$d_6$) δ 9.59 (s, 1H), 7.88 (d, J=8.4 Hz, 2H), 7.68–7.56 (m, 3H), 7.47 (d, J=8.4 Hz, 2H), 7.42–7.39 (m, 1H), 7.19–7.11 (m, 3H), 5.17 (q, J=6.9 Hz, 1H), 4.90 (m, 1H), 3.88 (s, 3H), 3.63 (s, 3H), 3.29 (dd, J=8.7 and 15.9 Hz, 1H), 2.81–2.26 (m, 8H), 1.25 (t, J=7.8 hz, 3H); HRMS (FAB) m/e calcd. for $C_{30}H_{33}N_2O_8S$ (MH$^+$) 581.1958; obsd. 581.1958.

Preparation 9
Synthesis of Compound 25

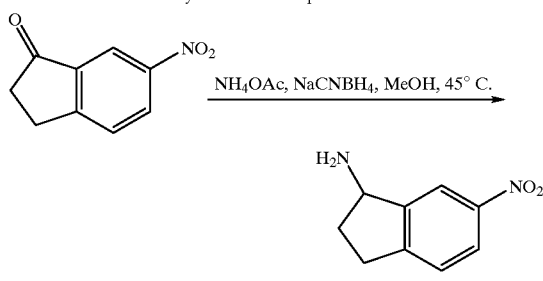

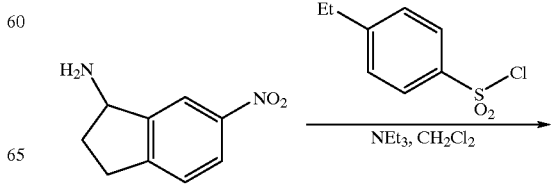

To a solution of 6-nitro-1-indanone (2.0 g, 12 mmol) in MeOH (25 mL) was added $NH_4OAc$ (9.4 g, 10 eq) followed by $NaCNBH_3$ (830 mg, 1.1 eq). The mixture was stirred at 45° C. for 40 h and then filtered (celite). The solvent was removed and to the resulting residue was added water (60 mL) and $Et_2O$ (60 mL). The aqueous layer was separated, treated with 6 N NaOH (24 mL), saturated with NaCl, and extracted with $CHCl_3$ (1×60 mL then 3×30 mL). The combined $CHCl_3$ layers was dried ($Na_2SO_4$), filtered and treated with 4 N HCl/dioxane (2 mL, 0.6 eq). Removal of the solvent provided a solid which was stirred with dry $Et_2O$ (120 mL, 1 h) and filtered. The HCl salt of the product was thus obtained as a solid (900 mg, 35%) and used in the next step without further purification. $R_f$ (silica gel): 0.13 (1% AcOH, 9% MeOH, 90% $CHCl_3$). $^1H$ NMR (300 MHZ, $CD_3OD$) δ 8.47 (d, J=1.7, 1H), 8.25 (dd, J=2.1, 8.4, 1H), 7.59 (d, J=8.4, 1H), 4.90–5.10 (m, 1H, solvent interference), 3.20–3.35 (m, 1H), 3.05–3.20 (m, 1H), 2.65–2.80 (m, 1H), 2.15–2.30 (m, 1H). $^{13}C$ NMR (75 MHZ, $CD_3OD$) δ 152.10, 147.60, 140.26, 125.96, 124.55, 119.78, 54.71, 30.23, 29.73.

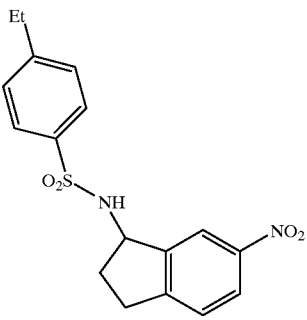

To a suspension of the hydrochloride salt of 1-amino-6-nitroindane (900 mg, 4.2 mmol) in dry $CH_2Cl_2$ (8 mL) was added $NEt_3$ (1.4 mL, 2.4 eq). The resulting homogeneous mixture was then treated with the sulfonyl chloride (940 mg, 1.1 eq) and stirred for 3 h. The resulting heterogeneous mixture was diluted with $CH_2Cl_2$ (8 mL), water (8 mL), and sat. aqueous $NH_4Cl$ (4 mL). The aqueous layer was separated and extracted with $CH_2Cl_2$ (3×4 mL). The combined organic layers was dried ($Na_2SO_4$), filtered, and treated with silica gel (4 g). Removal of the solvent provided a solid which was applied to a column of silica gel (1.5"×9.5") and purified by flash chromatography. Removal of the solvent provided the product as a solid (1.28 g, 88%). $R_f$ (silica gel): 0.29 (30% EtOAc, 70% hexanes). $^1H$ NMR (300 MHZ, $CDCl_3$) δ 7.98 (dd, J=1.9, 8.2, 1H), 7.70–7.85 (m, 3H), 7.25–7.40 (m, 3H), 5.77 (d, J=9.2, 1H), 4.82 (dd, J=7.9, 16.3, 1H), 2.85–3.00 (m, 1H), 2.65–2.85 (m, 3H), 2.25–2.40 (m, 1H), 1.75–1.90 (m, 1H), 1.26 (t, J=7.6, 3H). $^{13}C$ NMR (75 MHZ, $CDCl_3$) δ 150.45, 149.64, 147.39, 144.16, 137.88, 128.82, 127.04, 125.32, 123.66, 119.62, 57.85, 34.36, 29.92, 28.60 14.78.

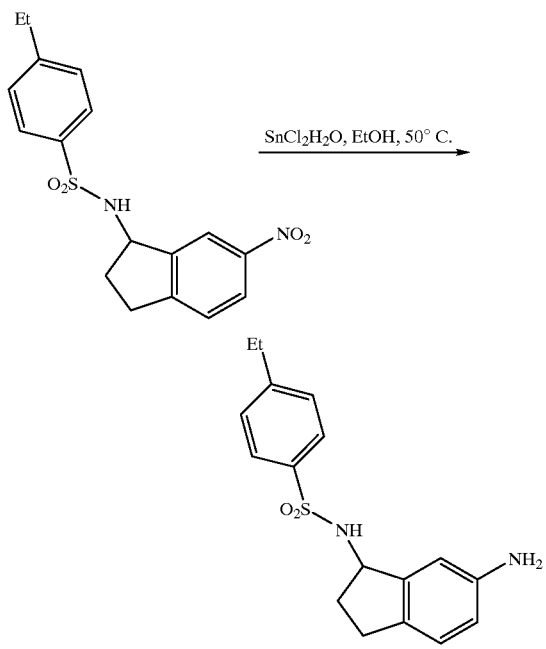

The 6-nitroindane derivative (1.09 g, 3.15 mmol) and $SnCl_2H_2O$ (3.6 g, 5 eq) were heated at 50° C. in absolute EtOH (7 mL) for 12 h. Most of the EtOH was removed and the resulting residue diluted with $CH_2Cl_2$ (30 mL), water (30 mL), and sat. aqueous $NaHCO_3$ (30 mL). After stirring for 30 min, the aqueous layer was separated and extracted with $CH_2Cl_2$ (3×30 mL). The combined organic layers was dried ($Na_2SO_4$), filtered, and treated with silica gel (2 g). Removal of the solvent provided a solid which was applied to a column of silica gel (1.0"×11") and purified by flash chromatography. Removal of the solvent provided the product as a solid (906 mg, 91%). $R_f$ (silica gel): 0.16 (15% EtOAc, 35% Hexanes, 50% $CH_2Cl_2$). $^1H$ NMR (300 MHZ, $CDCl_3$) δ 7.84 (2H), 7.35 (2H), 6.93 (1H), 6.53 (1H), 6.39 (1H), 5.20 (1H), 4.70 (1H), 3.51 (2H), 2.50–2.85 (4H), 2.24 (1H), 1.66 (1H), 1.28 (3H). $^{13}C$ NMR (75 MHZ, $CDCl_3$) δ 149.52, 145.46, 143.37, 138.52, 132.53, 128.60, 127.24, 125.20, 115.55, 110.73, 58.57, 34.72, 28.92, 28.62, 15.01. HRMS (FAB) m/e calcd. for $C_{17}H_{20}N_2O_2S$ (M) 316.1245, obsd. 316.1245.

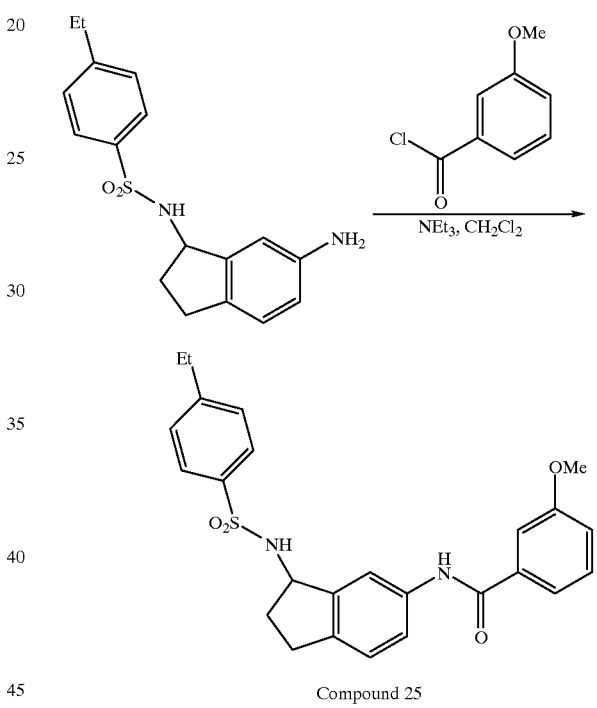

Compound 25

To a solution of the 6-aminoindane derivative (200 mg, 0.63 mmol) in dry $CH_2Cl_2$ (3 mL), was added the acid chloride (120 mg, 1.1 eq) followed by $NEt_3$ (0.1 1 mL, 1.2 eq). The mixture was allowed to stir O/N and then diluted with water (6 mL), sat. aqueous $NH_4Cl$ (1 mL) and $CHCl_3$ (100 mL). The $CHCl_3$ layer was separated, dried ($Na_2SO_4$), and filtered. Removal of the solvent provided a solid which was washed with $Et_2O$. In this way the product was obtained as a white solid (260 mg, 92%). $R_f$ (silica gel): 0.28 (15% EtOAc, 35% Hexanes, 50% $CH_2Cl_2$). $^1H$ NMR (300 MHZ, DMSO-d6) δ 10.18 (s, 1H), 8.07 (d, J=9.1, 1H), 7.78 (d, J=8.1, 2H), 7.69 (s, 1H), 7.62 (d, J=8.1), 7.35–7.55 (m, 5H), 7.10–7.20 (m, 2H), 4.60–4.75 (m, 1H), 3.83 (s, 3H), 2.50–2.80 (m, 4H), 1.80–1.95 (m, 1H), 1.45–1.60 (m, 1H), 1.18 (t, J=7.6, 3H). HRMS (FAB) m/e calcd. for $C_{25}H_{27}N_2O_4S$ ($MH^+$) 451.1691, obsd. 451.1692.

Preparation 10
Synthesis of the Cis Analog of Compound 4

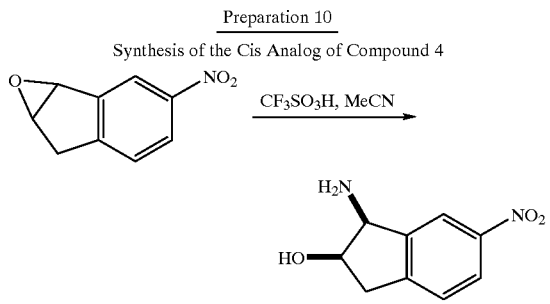

Trifluoromethanesulphonic acid (0.73 ml, 8.3 mmol) was added dropwise to a slurry of 5-nitroindene oxide (735 mg, 4.15 mmol) in CH$_3$CN (6.8 mL) at -40° C. After 30 min, the reaction mixture was allowed to warm to rt over 1 h and then water (4 mL) was added. After stirring for 10 minutes, the acetonitrile was removed by atmospheric distillation (pot temperature 100° C.). The aqueous residue was maintained at 100° C. for an additional 5 h and then cooled to rt. The aqueous phase was extracted with CH$_2$Cl$_2$ (10 mL) then basified with 1 N NaOH to pH 13 and extracted with CH$_2$Cl$_2$ (3×10 mL). The organics were combined, dried (Na$_2$SO$_4$), and concentrated under reduced pressure. Flash chromatography (5% MeOH/95% EtOAc) of the residue afforded the cis amino alcohol as a brown solid (518 mg, 64%). $^1$H NMR (300 MHZ, CDCl$_3$) δ 8.17 (s, 1H), 8.13 (d, J=7.1 Hz, 1H), 7.38 (d, J=8.1 Hz, 1H), 4.50–4.45 (m, 1H), 4.45–4.40 (m, 1H), 3.52–3.49 (m, 1H), 3.17–3.03 (m, 1H), 1.43 (s, 9H). This product was converted to the cis-analog of compound 4 using procedures described in the synthesis of compound 4.

Preparation 11
Synthesis of Compound 21

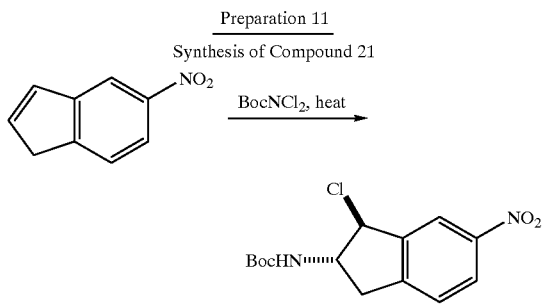

A solution of 5-nitroindene (800 mg, 4.97 mmol) and tert-Butyl N,N-dichloro-carbamate (924 mg, 4.97 mmol) in toluene (10 mL) was heated at 50° C. for 5 h. The resulting solution was cooled to 0° C. and stirred with a saturated solution of sodium metabisulfite (10 mL) for 20 min. The organics were extracted with ether (2×10 mL), dried (Na$_2$SO$_4$), and concentrated under reduced pressure. Flash chromatography (80% hexanes/20% Et$_2$O) of the residue afforded the desired product as a colorless oil (312 mg, 22%). $^1$H NMR (300 MHZ, CDCl$_3$) δ 8.27 (s, 1 H), 8.17 (dd, J=8.3, 2.0 Hz, 1H), 7.40 (d, J=8.4 Hz, 1H), 5.28 (bs, 1H), 4.84 (bs, 1H), 4.45 (m, 1H), 3.52 (dd, J=17.0, 7.3 Hz, 1H), 3.04–2.98 (m, 1H), 1.46 (s, 9H).

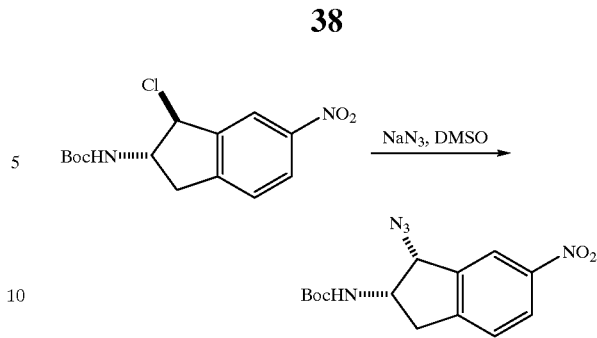

Sodium azide (222 mg, 3.43 mmol) was added to a stirring solution of nitroindane derivative (715 mg, 2.28 mmol) in DMSO (3 mL) at rt. The resulting purple solution was heated at 50° C. for 14 h, cooled to rt and diluted with water (5 mL). The organics were extracted with EtOAc (4×5 mL), dried (Na$_2$SO$_4$), and concentrated under reduced pressure. Flash chromatography (80% hexanes/20% Et$_2$O) of the residue afforded the desired product as a colorless oil (675 mg, 68%). $^1$H NMR (300 MHZ, CDCl$_3$) δ 8.17 (s, 1H), 8.13 (m, 1H), 7.38 (d, J=8.1 Hz, 1H), 5.74 (bs, 1H), 4.93 (d, J=5.9 Hz, 1H), 4.61–4.50 (m, 1H), 3.20 (dd, J=16.6, 7.4 Hz, 1H), 2.92 (dd, J=16.6, 9.0 Hz, 1H), 1.43 (s, 9H).

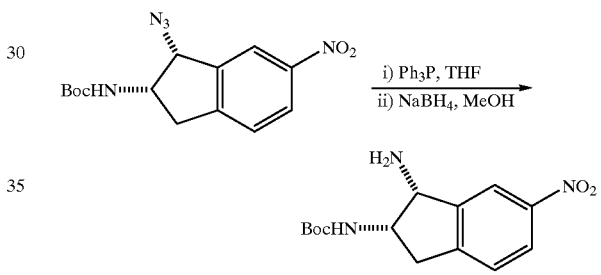

Triphenylphosphine (270 mg, 1.03 mmol) was added to a stirring solution of azidonitroindane derivative (300 mg, 0.94 mmol) in THF (4 mL) at rt. After 1 h, the solvent was removed under reduced pressure and replaced with MeOH (4 mL). The new solution was cooled to 0° C. and sodium borohydride (36 mg, 0.94 mmol) was added portionwise. After 30 min at 0° C. 5 drops of glacial acetic acid were added. The reaction was concentrated to dryness and taken up in EtOAc (20 mL). The organic phase was washed with 1 N HCl (2×10 mL) and the aqueous phase was basified to pH 11 with 1 N NaOH and re-extracted with EtOAc (3×10 mL). The organics were combined, dried (Na$_2$SO$_4$), and concentrated under reduced pressure to afford the desired product as a pale brown solid (196 mg, 71%). $^1$H NMR (300 MHZ, CDCl$_3$) δ 8.17 (s, 1H), 8.06 (dd, J=8.2, 1.9 Hz, 1H), 7.32 (d, J=8.3 Hz, 1H), 5.27 (bs, 1H), 4.41 (bs, 2H), 3.28–3.21 (m, 1H), 2.94–2.87 (m, 1H), 1.42 (s, 9H).

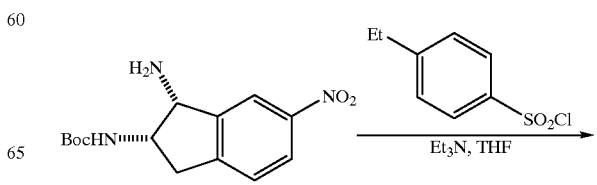

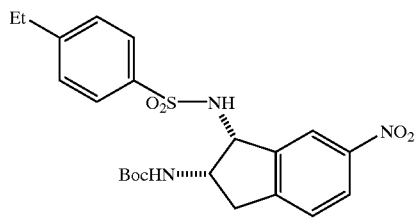

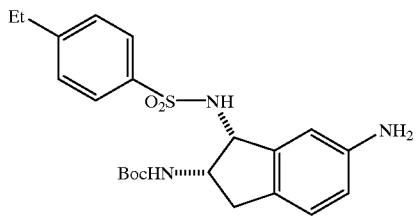

p-Ethylsulphonylchloride (240 mg, 1.17 mmol) was added to a stirring solution of aminonitroindane derivative (330 mg, 1.12 mmol) and triethylamine (171 µL, 1.23 mmol) in THF (5 mL) at 0° C. The reaction was then heated at 50° C. for 2 h, cooled and EtOAc (15 mL) was added. The organics were washed with brine (10 mL), dried ($Na_2SO_4$), and concentrated under reduced pressure. Flash chromatography (50% hexanes/50% $Et_2O$) of the residue afforded the desired product as a white solid (247 mg, 48%). $^1$H NMR (300 MHZ, $CDCl_3$) δ 8.07 (d, J=8.4, 2.1 Hz, 1H), 7.77 (d, J=8.0 Hz, 2H), 7.39–7.31 (m, 4H), 5.20–4.98 (m, 2H), 4.81–4.73 (m, 1H), 4.44 (p, J=6.7 Hz, 1H), 3.25 (dd, J=16.7, 6.5 Hz, 1H), 2.89 (dd, J=17.2, 6.4 Hz, 1H), 2.72 (q, J=7.5 Hz, 2H), 1.45 (s, 9H), 1.29 (t, J=7.6 Hz, 3H).

Sodium borohydride (68 mg, 1.7 mmol) was added portionwise to a stirring suspension of nitroindane derivative (168 mg, 0.36 mmol) and nickel chloride (10 mg, 0.08 mmol) in THF/methanol (1:1, 3 mL) at 0° C. After 20 min, the reaction mixture was quenched with water (5 mL), extracted with EtOAc (3×10 mL), dried ($Na_2SO_4$), and concentrated under reduced pressure to afford the desired product as a pale brown solid (156 mg, 99%). $^1$H NMR (300 MHZ, $CDCl_3$) δ 7.81 (d, J=8.3 Hz, 1H), 7.36 (d, J=8.1 Hz, 1H), 6.92 (d, J=7.9 Hz, 1H), 6.53 (d, J=7.0 Hz, 1H), 6.11 (bs, 1H), 5.04–4.92 (bs, 2H), 4.63–4.55 (bs, 1H), 4.32–4.24 (m, 1H), 3.04–2.94 (m, 1H), 2.75 (q, J=7.5 Hz, 2H), 2.68–2.55 (m, 1H), 1.43 (s, 9H), 1.25 (t, J=7.5 Hz, 3H).

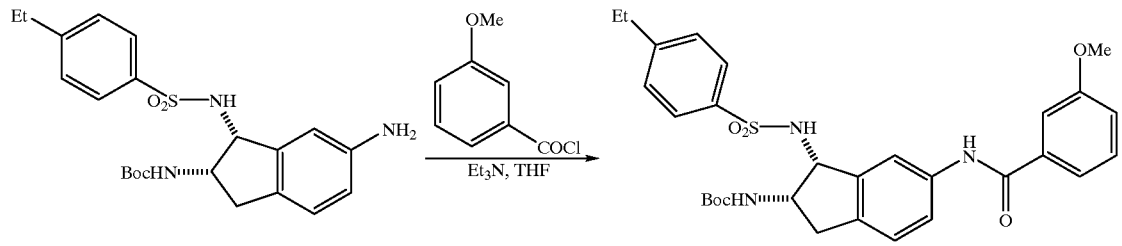

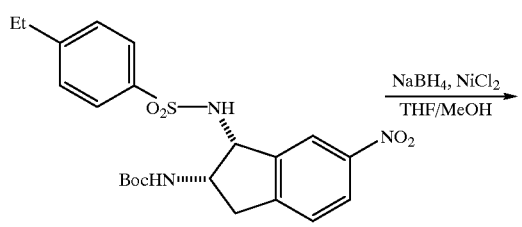

m-Anisoylchloride (6.5 µL, 0.046 mmol) was added to a stirring solution of aminoindane derivative (20 mg, 0.046 mmol) and triethylamine (7.7 µL, 0.055 mmol) in THF (3 mL) at 0° C. After 30 min, the reaction mixture was diluted with EtOAc (10 mL), washed with brine (10 mL), dried ($Na_2SO_4$), and concentrated under reduced pressure. Flash chromatography (50% hexanes/50% EtOAc) of the residue afforded the desired product as a white solid (22 mg, 84%). $^1$H NMR (300 MHZ, $CDCl_3$) δ 7.84 (d, J=8.4 Hz, 2H), 7.70–7.61 (m, 2H), 7.40–7.34 (m, 4H), 7.18 (d, J=8.1 Hz, 1H), 7.11–6.91 (m, 2H), 4.98 (d, J=8.0 Hz, 1H), 4.98–4.90 (bs, 1H), 4.69 (t, J=7.0 Hz, 1H), 4.39–4.30 (m, 1H), 3.89 (s, 3H), 3.14 (dd, J=15.9, 6.7 Hz, 1H), 2.76 (dd, J=15.9, 5.1 Hz, 1H), 2.71 (q, J=7.7 Hz, 2H), 1.44 (s, 9H), 1.24 (t, J=7.6 Hz, 3H).

Compound 21

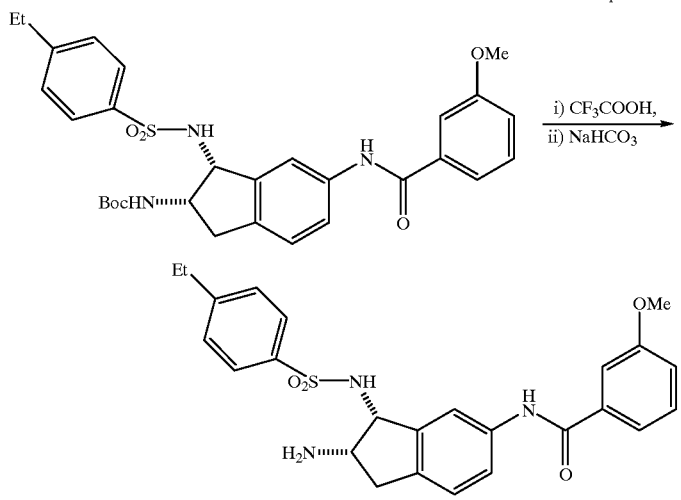

Trifluoroacetic acid (0.5 ml) was added to a stirring solution of the intermediate (22 mg, 0.04 mmol) in $CH_2Cl_2$ (2 mL) at 0° C. The ice bath was removed and the reaction was allowed to warm to rt over 1 h. The solvent was removed under reduced pressure and replaced with EtOAc (5 mL). A saturated aqueous solution of $NaHCO_3$ was added to the organic solution and the biphasic system was stirred vigorously for 30 min. The organic layer was separated, dried $Na_2SO_4$), and concentrated under reduced pressure to afford the desired product as a off-white solid (11 mg, 61%). $^1H$ NMR (300 MHZ, DMSO-$d_6$) δ 10.1 (s, 1H), 7.81 (d, J=8.1 Hz, 2H), 7.69–7.40 (m, 7H), 7.15–7.11 (m, 2H), 5.73 (s, 2H), 4.53 (d, J=5.6 Hz, 1H), 3.83 (s, 3H), 2.85 (dd, J=15.8, 6.2 Hz, 1H), 2.65 (q, J=7.5 Hz, 2H), 2.53–2.44 (m, 1H), 1.16 (t, J=7.6 Hz, 3H).

Preparation 12

Synthesis of the Regioisomers of Compound 4

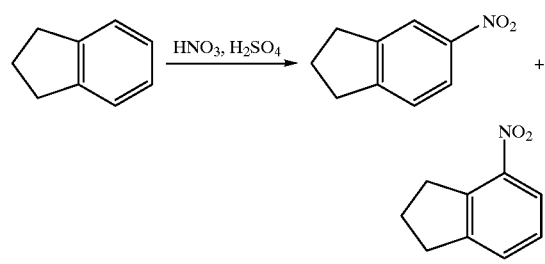

A solution of conc. $H_2SO_4$ (30 g) and conc. $HNO_3$ (10 g) was added dropwise over 2 h to a stirring solution of indane (10 g, 81.6 mmol) at −20 ° C. The resulting purple solution was then stirred for another hour after which water (20 g) was added dropwise. The organics were extracted with EtOAc (3×20 mL), dried ($Na_2SO_4$), and concentrated under reduced pressure. Flash chromatography (80% hexanes/20% $Et_2O$) of the residue afforded a 2:3 mixture of the two products (5.33 g, 37%) as a viscous oil. This material was used directly in the next step without further purification.

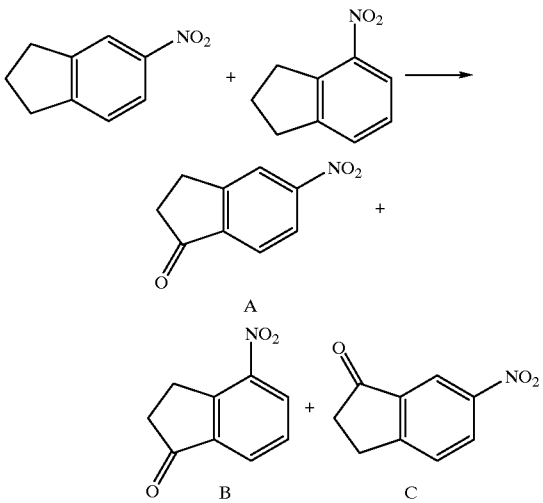

A solution of $CrO_3$ (7.59 g, 75.9 mmol) in 50% aqueous acetic acid (84 mL) was added dropwise to a stirring solution of the two nitroindanes (3.0 g, 18.4 mmol) in acetic acid (75 mL) at rt. After the addition, stirring was continued for an additional 24 h. Isopropyl alcohol (50 mL) was then slowly added and the green mixture was stirred for 30 min at rt. The organics were extracted with $Et_2O$ (4×20 mL), dried ($Na_2SO_4$), and concentrated under reduced pressure. Flash chromatography (30% EtOAc/70% hexanes to 50% EtOAc/50% hexanes) afforded three separate compounds in a 3:3:1 (A:B:C) ratio in a combined yield of 22%. $^1H$ NMR of compound A (300 MHz, $CDCl_3$) δ 8.36 (d, J=2.0 Hz, 1H), 8.25 (dd, J=7.0, 2.0 Hz, 1H), 7.92 (d, J=7.0 Hz, 1H), 3.32–3.27 (m, 2H), 2.88–2.83 (m, 2H).

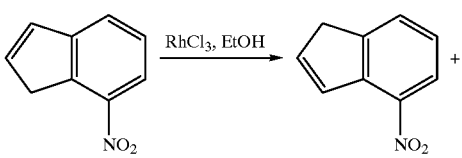

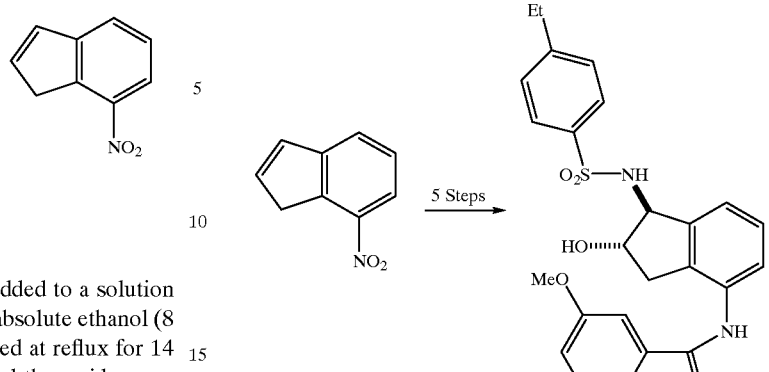

Rhodium trichloride (1 mg, cat.) was added to a solution of 7-nitroindene (150 mg, 0.93 mmol) in absolute ethanol (8 mL) at rt. The resulting solution was heated at reflux for 14 h after which the solvent was removed and the residue was purified by flash chromatography (5% Et$_2$O/95% hexanes) to afford the desired product (64 mg, 43%) as a pale brown solid and starting material (76 mg, 51%). $^1$H NMR of product (300 MHZ, CDCl$_3$) δ 8.15 (d, J=6.6 Hz, 1H), 7.74–7.70 (m, 2H), 7.34 (t, J=6.6 Hz, 1H), 6.95–6.90 (m, 1H), 3.54 (s, 2H).

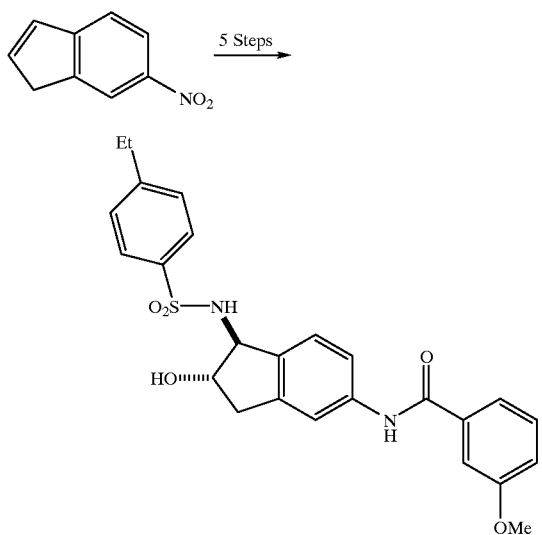

This regioisomer of compound 4 was synthesized following the same general procedure used for the preparation of compound 4. $^1$H NMR (300 MHZ, CD$_3$OD) δ 8.24 (d, J=8.4 Hz, 1H), 7.81 (d, J=8.2 Hz, 2H), 7.59 (d, J=1.1 Hz, 1H), 7.50–7.36 (m, 6H), 7.09 (dd, J=8.1, 2.5 Hz, 1H), 6.66 (d, J=8.3 Hz, 1H), 5.10 (bs, 1H), 4.36 (dd, J=8.1, 5.1 Hz, 1H), 4.10 (q, J=6.0 Hz, 1H), 3.82 (s, 3H), 3.07 (dd, J=15.8, 6.6 Hz, 1H), 2.70 (q, J=7.5 Hz, 2H), 2.59 (dd, J=15.6, 5.8 Hz, 1H), 1.23 (t, J=7.5 Hz, 3H).

This regioisomer of compound 4 was synthesized following the same general procedure used for the preparation of compound 4. $^1$H NMR (300 Hz, CDCl$_3$) δ 7.91 (d, J=8.3 Hz, 3H), 7.61(s, 1H), 7.42–735 (m, 5H), 7.22 (t, J=7.9 Hz, 2H), 7.10 (dd, J=7.9, 1.38 Hz, 1H), 6.72 (d, J=7.4 Hz, 1H), 5.02 (d, J=7.5 Hz, 1H), 4.56–4.51 (m, 2H), 3.87 (s, 3H), 3.38 (s, 1H), 3.25 (dd, J=15.7, 7.7 Hz, 1H), 2.81–2.72 (m, 3H), 1.28 (t, J=7.5 Hz, 3H).

BioAssays

1. Cloning, Construction and Testing of CHO Cells that Express Human Voltage-gated Potassium Channels Human voltage-gated potassium channels were cloned from genomic HeLa cellular DNA by polymerase chain reaction (PCR), sequenced to verify their composition, and then expressed permanently in Chinese Hamster Ovary (CHO) cell lines (obtained from ATCC) using methods well known to those skilled in the art.

Specifically, HeLa cells (approximately 1000 cells) were washed in phosphate-buffered saline, pelleted, and lysed in 50 μl of sterile water. PCR reagents including specific end primers were added directly to the lysate and the mixture subjected to 40 temperature cycles. Products of the reaction were separated on an agarose gel and a DNA band corresponding to the expected size of the amplified product was isolated and subcloned into the cloning vector pCRII (Invitrogen). The construct was amplified in E. coli and a number of independent subclones isolated and sequenced to verify the identity of the cloned channel. Error-free parts of these clones were then ligated together to form a complete cDNA construct, and this construct subcloned into the eukaryotic expression vector pCDNA3 (Invitrogen). The completed construct contained a Kozak sequence at the start to direct protein synthesis. CHO cells were transfected with the construct and stable, expressing cells were selected by including G418 in the culture medium. After 3 weeks, stably transfected cells were seeded at limiting density and single clones isolated and grown to confluence.

Stable clones were tested for voltage-gated potassium channel expression using a $^{86}$rubidium ($^{86}$Rb) ion flux assay (see below for methodology). In the case of the potassium channel Kv1.3, four positive clones and one negative control were tested in the rubidium efflux assay for inhibition of efflux by margatoxin, a known selective blocker of Kv1.3 channels. All positive clones exhibited a KCl-stimulated $^{86}$Rb efflux between 7 to 10-fold over basal, which was inhibited at a level of approximately 95% when margatoxin was present. These clones were tested further by electrophysiology, and were clearly shown to possess properties consistent with the expression of the potassium channel.

2. $^{86}$Rubidium Efflux From Cell Monolayers

CHO cells stably transfected with either human Kv1.5 or Kv1.3 as well as nontransfected cells were grown to approximately 90% confluence in 24 well tissue culture plates. Tissue culture growth medium was then removed and replaced with 1 ml of Iscoves modified DMEM containing $^{86}$Rb at a concentration of 1 $\mu$Ci/ml and incubated for three hours at 37° C. to permit intracellular uptake of the isotope. At the end of the incubation period, the $^{86}$Rb solution was aspirated and the cells washed three times with Earls Balanced Salt Solution (EBSS). The cells were then incubated for 15 minutes at room temperature in 0.6 ml/well of EBSS or EBSS containing the compounds to be tested. At the end of this period, a 0.3 ml sample was taken for analysis to determine basal efflux of $^{86}$Rb. To each well was then added 0.3 ml of a modified high KCl EBSS, containing 125 mM KCl (NaCl replaced by KCl; final KCl concentration in each well was 65 nM) and the compounds to be tested. The high KCl concentration was utilized to depolarize the cells to membrane potentials that would activate Kv1.3 and Kv1.5 channels. After a 15 minute incubation, another 0.3 ml sample was taken for analysis. Finally 0.3 ml of 0.2% sodium dodecyl sulfate in EBSS was added to each well to lyse the cells. Of this lysate 0.3 ml was taken for analysis to determine final cell content of $^{86}$Rb. Samples were counted in a Wallac Microbeta Liquid Scintillation counter by Cerenkov emission. Efflux was expressed as a percentage of the initial cell content of $^{86}$Rb.

3. Fluorescence Measurement of Cell Membrane Potential

CHO cells stably transfected with genes encoding human voltage gated potassium channels were grown to 80–90% confluency in 96 well tissue culture plates. On the experimental day, they were repeatedly contacted with a modified EBSS (116 mM NaCl, 5.4 mM KCl, 1.8 mM CaCl$_2$, 0.8 mM MgCl$_2$, 20 mM HEPES, 5 nM glucose; pH 7.4, 300 mOsm) plus 5 $\mu$M of the voltage-sensitive oxonol dye, bis-(1,3-dibutylbarbituric acid)trimethine oxonol (DiBac$_4$(3)). Dibac$_4$(3) binds to intracellular proteins in a membrane potential-dependent process, changing the effective concentration of fluorescing molecules. An increase in fluorescence is indicative of membrane depolarization, while a decrease in fluorescence indicates membrane hyperpolarization (Epps et al., *Chemistry and Physics of Lipids,* 69:137, 1994). The cells in each well were then incubated in EBSS+5 $\mu$M DiBac$_4$(3) at 37° C. for 30 minutes. The 96 well plate was then placed in a 35° C. temperature controlled chamber within a laser based fluorescence imaging plate reader (NovelTech Inc.). Data were collected every 60 seconds for periods ranging from 20 to 40 min. To permit comparative quantification of the magnitude of drug induced changes in the fluorescence signal, changes were compared to the addition of EBSS+5 $\mu$M DiBac$_4$ (3) without drug and EBSS+5 $\mu$M DiBac$_4$(3)+30 mM KCl without drug, and expressed as a percentage of the increase in fluorescence induced by exposure of the cells to 30 mM KCl. (Elevation of extracellular KCl is known to depolarize cells.) For effective utilization of DiBac$_4$(3) in the assays described above, contact of dye-containing solutions with plastics and proteins was minimized.

4. Electrophysiological Studies

Electrophysiological recordings of native channels in cells and cell lines, cloned and expressed channels in cells (e.g., CHO cells) as well as isolated cardiac myocytes were performed using the whole cell configuration of the patch clamp technique (Hamill et al., *Pflugers Archiv* 391:85, 1981). Cell lines were prepared as described above (cloning, etc.). Rat and human cardiac myocytes were isolated using the methods described in Castle and Slawsky, *J. Pharmacol. Exp. Ther.* 264:1450, 1993 and Wang et al., *Circ. Res.,* 73:1061, 1993, respectively. Cells were plated on glass coverslips at a density of 2×10$^4$ cells/coverslip and used within 24–48 hours for cultured cell lines and within 6 hours for isolated cardiac myocytes. The coverslips were placed in a small chamber (volume ~200 $\mu$l) on the mechanical stage of an inverted microscope and perfused (2 ml/min) with extracellular recording solution. Drug application was achieved via a series of narrow-bore glass capillary tubes (inner diameter ~100 $\mu$m) positioned approximately 200 $\mu$m from the cell. Application of voltage-clamp pulses, data acquisition and the analysis were controlled by a 75 MHz Pentium computer using pCLAMP 6.0 software (Axon Instruments Inc. Foster City, Calif.).

5. Lymphocyte Proliferation Studies

A T-lymphocyte proliferation assay was performed using human peripheral T-lymphocytes isolated by centrifugation on lymphocyte separation medium (Organon Teknika) followed by adherence of non-T cells on nylon wool. (Following isolation, T-lymphocytes were found to have >98% viability by trypan blue dye exclusion.) Cells were resuspended in RPMI medium supplemented with 10% fetal bovine serum at a concentration of 1×10$^6$ cells/ml. 100 $\mu$l of cells/well was dispensed into a 96-well plate. Cells were stimulated with phytohemoagglutinin (1.25 or 2.5 $\mu$g/ml final concentration) in the presence or absence of various antagonists for 3 days. On the fourth day, cells were pulsed with [$^3$]thymidine for an additional 18 hours and harvested on glass fiber filtermats with extensive washing. Mats were counted in a Wallac Microbeta liquid scintillation counter using melt-on scintillant. Additional wells were counted at the end of the 18 hour period to determine if the drug treatments caused cellular toxicity.

EXAMPLE 1

Effect of compound 4 on membrane potential in cell monolayers.

Inhibition of voltage-gated potassium channels by compound 4 and related molecules was initially assessed by their ability to induce cell membrane depolarization in monolayers of CHO cells permanently transfected with cDNA for human Kv1.5 or Kv1.3 potassium channels. The actions of indane compound 4 and related molecules were compared with the effects of known inhibitors of Kv1.5 or Kv1.3 to alter membrane potential as detected with the voltage-dependent fluorescent dye Dibac$_4$ normalized to the depolarization induced by 30 nM KCl. By way of example, FIG. 1 illustrates the effect of compound 4 on membrane potential in monolayers of CHO cells expressing human Kv1.3, which at 10 $\mu$M, produced a depolarization similar in magnitude to that induced by the Kv1.3-specific blocking toxin margatoxin. Values are means ±s.e. from four observations. Addition of agents are indicated by arrows. Baseline fluorescence is shown by the open symbols. The compound 4 induced depolarization was absent in nontransfected cells.

EXAMPLE 2

Effect of compound 4 on $^{86}$Rubidium fluxes from cell monolayers expressing Kv1.5 or Kv1.3

Figure 2:
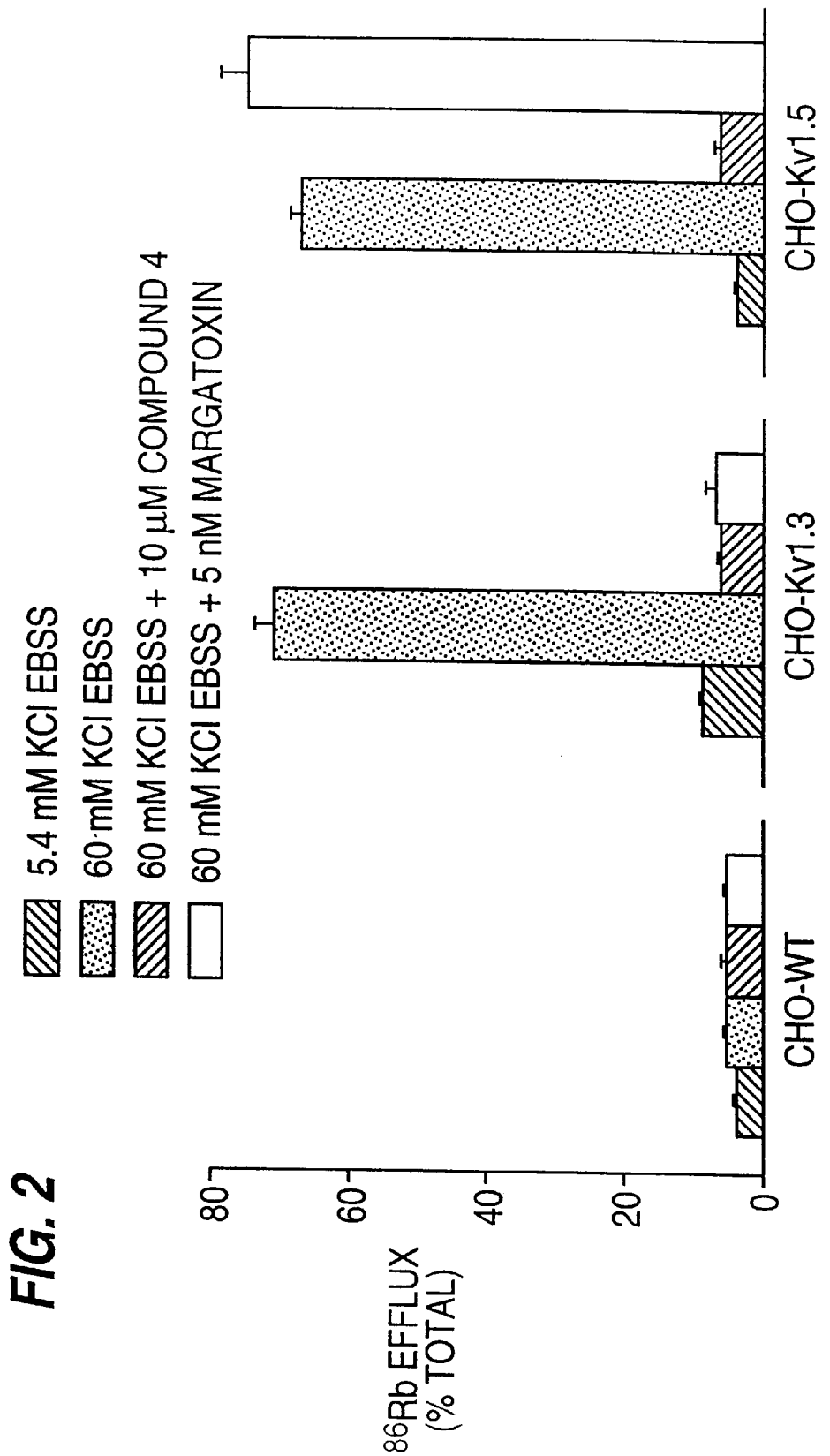
FIG. 2 compares the inhibitory effect of 10 μM of compound 4 on the increase in rubidium 86 ($^{86}$Rb) efflux evoked by 60 mM KCl in CHO cells expressing human Kv1.3 or Kv1.5 potassium channels.

The effect of compound 4 on the efflux of $^{86}$Rb from preloaded monolayers of CHO cells expressing either human Kv1.5 or Kv1.3 is shown in FIG. 2. Values are means ±s.e. (n=4) of the amount of $^{86}$Rb released in a 15 minute period and are expressed as a percentage of the initial cell content. The relationship between the KCl induced efflux and activation of Kv1.3 or Kv1.5 is supported by the observation that non-transfected CHO cells did not exhibit an increase in $^{86}$Rb efflux in the presence of KCl. The differential effect of 5 nM margatoxin confirmed channel specific activation of $^{86}$Rb efflux from CHO cells expressing Kv1.3 and Kv1.5. An increase in the rate of $^{86}$Rb efflux following exposure to 60 mM KCl occurred in cells expressing Kv1.5 and Kv1.3, but was absent in non-transfected (wild type) cells. In Kv1.3 expressing cells, the 60 mM KCl evoked increase in the $^{86}$Rb efflux rate could be completely abolished by preexposure to either 5 nM margatoxin or 10 $\mu$M compound 4. Similarly 10 $\mu$M compound 4 completely inhibited the 60 nM KCl evoked increase in the $^{86}$Rb efflux rate in CHO cells expressing Kv1.5.

EXAMPLE 3

Effects of compound 4 and related compounds on Kv1.5 and Kv1.3 potassium channels.

Figure 3:
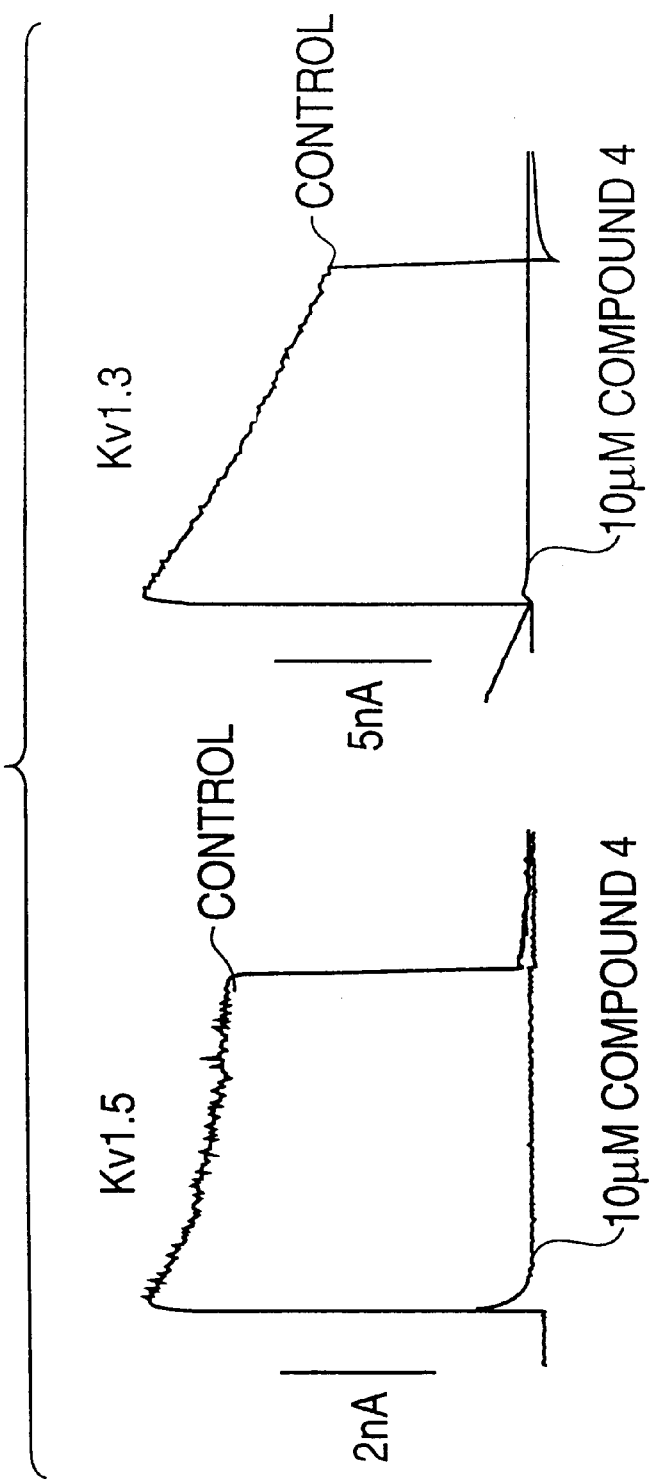
FIG. 3 illustrates inhibition of potassium currents by compound 4 in voltage-clamped CHO cells expressing Kv1.3 or Kv1.5.

Direct measurement of the inhibitory action of compound 4 and related compounds on ionic currents was measured using the whole cell patch clamping assay as has been described. By way of example, the inhibitory action of compound 4 on ionic currents through Kv1.5 and Kv1.3 channels in CHO cells is illustrated in FIG. 3. 500 ms voltage clamp steps from –80 mV to +60 mV were applied to individual cells every 20 seconds for Kv1.5 and every 60 seconds for Kv1.3. Current traces recorded in the absence of drug, and following a 5 min preincubation with 10 $\mu$M compound 4 are shown. The efficacy of compound 4 and representative structural homologs as inhibitors of Kv1.5 are shown in Table 1.

TABLE 1

| Compound | 50% Channel Inhibition (IC$_{50}$) |
| --- | --- |
| 4 | 0.1 $\mu$M (approx.) |
| 2 | 1 $\mu$M (approx.) |
| 16 | 1 $\mu$M (approx.) |
| 13 | 1 $\mu$M (approx.) |
| 11 | 1 $\mu$M (approx.) |
| 15 | 1 $\mu$M (approx.) |
| 17 | >1 $\mu$M (approx.) |
| 12 | >1 $\mu$M (approx.) |
| 10 | >1 $\mu$M (approx.) |

Other compounds illustrated as examples of Formulas (I), (I) and (III) exhibited IC$_{50}$ values greater than 5 $\mu$M but less than 50 $\mu$M.

EXAMPLE 4

Effect of Compound 4 on I$_{Kur}$ in human atrial myocytes

The delayed rectifier voltage-gated potassium channel responsible for the cardiac ionic current variously termed I$_{Kur}$ or I$_{sus}$ has been reported to contain the Kv1.5 $\alpha$-subunit gene product. I$_{Kur}$ (or I$_{sus}$) is generally believed to be important in the repolarization of the human atrial action potential (Wang et al., *Circ. Res.* 73:1061, 1993; Fedida et al., *Circ. Res.* 73:210, 1993; Wang et al., *J. Pharmacol. Exp. Ther.* 272:184, 1995). 1 $\mu$M of compound 4 was found to inhibit I$_{Kur}$ currents in isolated human atrial myocytes by >50%.

EXAMPLE 5

Effect of compound 4 on cardiac action potential

Figure 4:
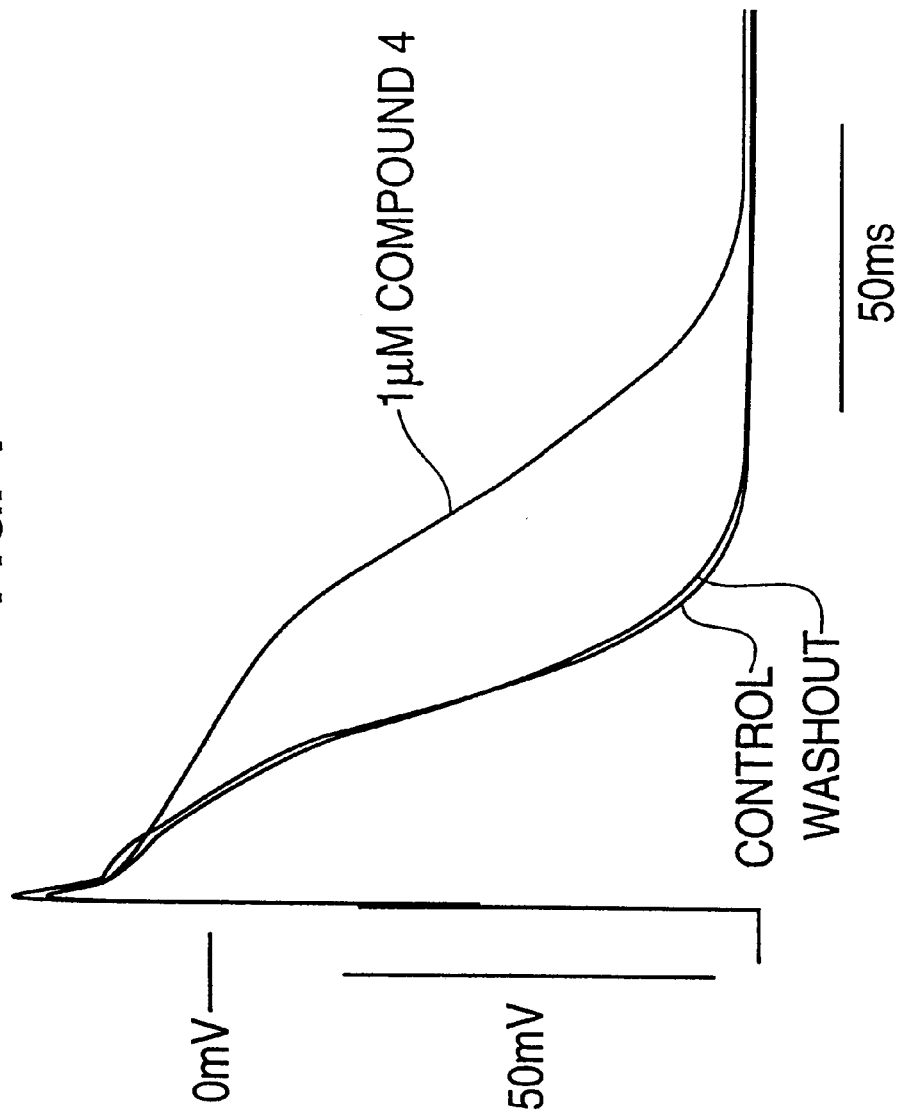
FIG. 4 shows action potentials elicited in a rat cardiac myocyte in the absence of drug (control), following a 2 min application of 1 μM of compound 4, and after washout of the drug.
Figure 5:
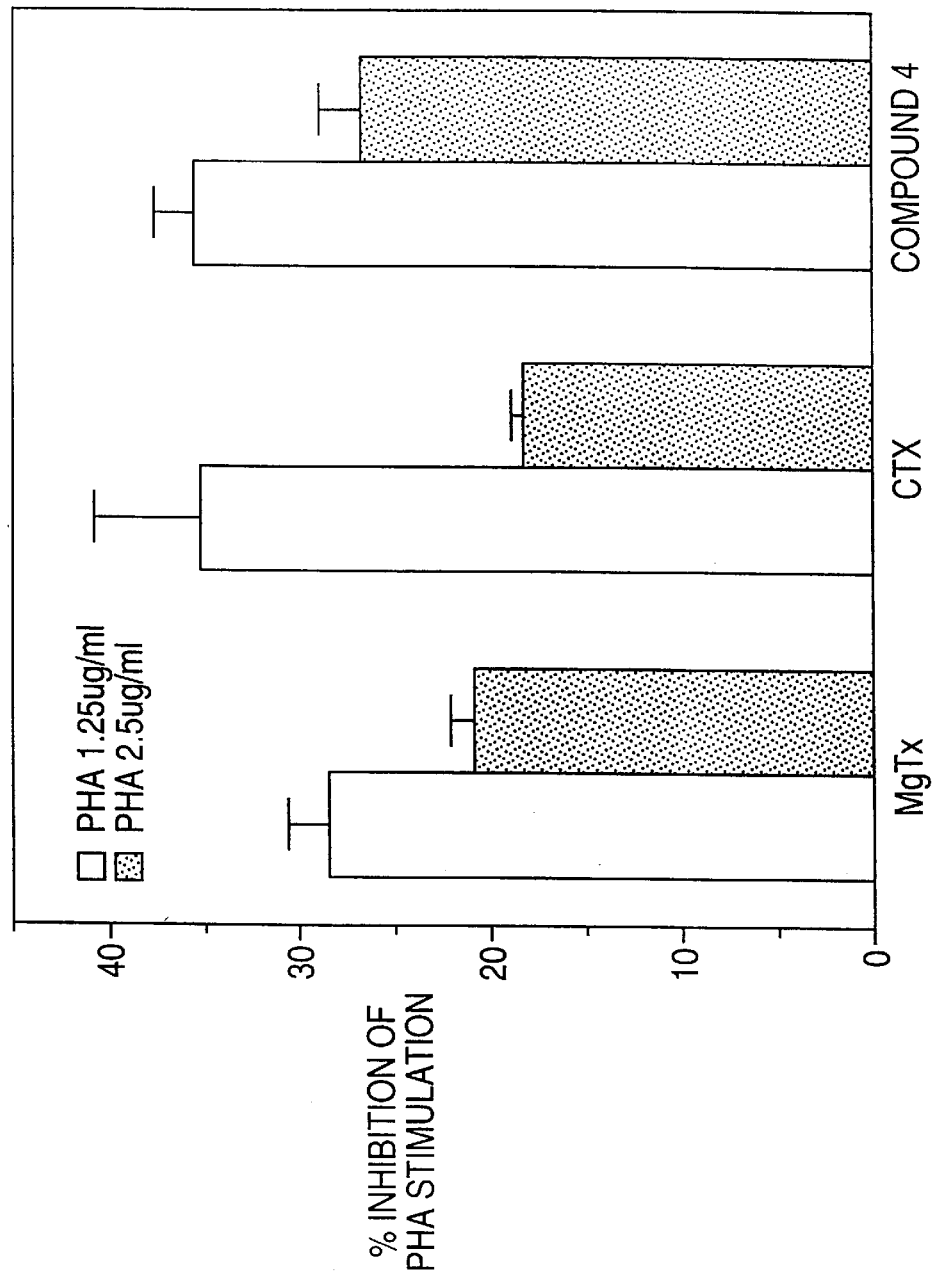
FIG. 5 compares the inhibitory effect of 10 μM of compound 4, 1 nM of margatoxin (MgTx), and 50 nM of charybdotoxin (CTX) on phytohemoagglutinin (PHA) (1.25 or 2.5 μg/ml) induced stimulation of $^3$H-thymidine incorporation into human T lymphocytes.

A functional consequence of potassium channel inhibition in the heart is a prolongation of the action potential duration. This increase in action potential duration, and resultant prolongation of the effective refractory period for propagating electrical excitability in the heart, mechanistically accounts for the antiarrhythmic properties of agents that block potassium channels. 1 $\mu$M of compound 4 prolongs the action potential by >50% in isolated human atrial myocytes. Similarly, FIG. 4 shows that 1 $\mu$M compound 4 prolongs the action potential in rat cardiac myocytes.

EXAMPLE 6

Lymphocyte proliferation assay of compound 4

A functional consequence of I$_{Kn}$ (Kv1.3) inhibition in human lymphocytes is an inhibition of antigen evoked cell proliferation (Chandy et al., *J. Exp. Med.* 160:369, 1984; Lin et al., *J. Exp Med.* 177:637, 1993). Such an action would therefore be immunosuppressive, yielding therapies for conditions in which immune cell activation and proliferation need to be prevented or treated. Compound 4 was tested in an in vitro lymphocyte proliferation assay to determine if its Kv1.3-blocking actions would lead to functional changes in a human cellular system. As shown in FIG. 4, margatoxin, charybdotoxin, and compound 4 all inhibited lymphocyte proliferation to a similar extent when compared to PHA-only controls. Compound 4 was not toxic to human T-lymphocytes, since after 90 hours of exposure to 10 $\mu$M of compound 4, there was no decrease in cell viability.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. Those skilled in the art will recognize variations in the processes as described above and will recognize appropriate modifications based on the above disclosure for making and using the compounds of the invention.

In the forgoing specification, the following abbreviations are used:

| Designation | Reagent or Fragment |
| --- | --- |
| m-CPBA | meta-chloroperoxybenzoic acid |
| Ac | Acetyl [CH$_3$C(O)—] |
| LC | liquid chromotagraphy |
| THF | tetrahydrofuran |
| TLC | Thin Layer Chromotagraphy |
| DMF | dimethylformamide |
| DMAP | para-dimethylaminopyridine |
| TEA | triethylamine |
| Me | methyl |
| Et | ethyl |
| EtOH | ethanol |
| Et$_2$O | diethyl ether |
| MeOH | methanol |
| EtOAc | ethylacetate |
| pTSA | para-toluene sulfonic acid |
| TsOH.H$_2$O | para-toluenesulfonic acid.water |
| PhMe | Toluene |
| I-PrOH | iso-propanol |
| AcOH | Acetic acid |
| NEt$_3$ | triethylamine |
| TFA | trifluoroacetic acid |

-continued

| Designation | Reagent or Fragment |
|---|---|
| (S,S)Mn-salem | (S,S)-N,N'-bis-(3,5-di-tert-butylsalycidene)-1,2-cyclo-hexanediaminomanganese (III) chloride |
| PPNO | 4-phenylpyridine-N-oxide |
| HOBt | 1-hydroxybenzotriazole |
| EDC | 1-(3-dimethylaminopropyl)-3-ethylcarbodiimide hydrochloride |
| 4-DMAP | 4-dimethylaminopyridine |
| NH$_4$OAc | Ammonium acetate |
| MeCN | acetonitrile |
| BocNCl$_2$ | tert-Butyl N,N-dichloro-carbamate |
| DMSO | dimethylsulfoxide |
| Ph$_3$P | triphenylphosphine |
| Dibac$_4$ | bis-(1,3-dibutylbarbituric acid)trimethine oxonol |
| rt | room temperature |

We claim:

1. A compound having potassium channel inhibitory activity of the formula:

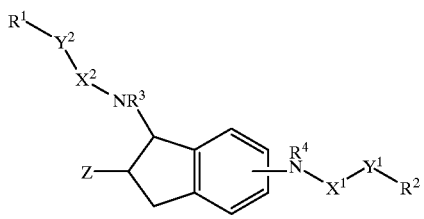

wherein,
R$^1$ is H, alkyl or is selected from the group consisting of an optionally substituted aryl, an optionally substituted heteroaryl, an optionally substituted heterocyclyl and an optionally substituted carbocycloalkyl;
R$^2$ is selected from the group consisting of alkyl, an optionally substituted aryl, an optionally substituted heteroaryl, an optionally substituted heterocyclyl and an optionally substituted carbocycloalkyl;
R$^3$ is hydrogen or methyl;
R$^4$ is hydrogen or methyl;
X$^1$ is C=O, C=S, or SO$_2$;
X$^2$ is C=O or SO$_2$;
Y$^1$ is O, (CH$_2$)$_p$, CH$_2$O, HC=CH or NH; wherein p is 0, 1 or 2;
Y$^2$ is O, (CH$_2$)$_q$, HC=CH or NH; wherein q is 0 or 1;
Z is H, OR$^5$ or NR$^6$R$^7$;
wherein
R$^5$ is H, (CH$_2$)$_m$—R$^8$; or C(O)—(CH$_2$)$_m$—R$^8$; m=1 to 5;
R$^8$ is N(R$^9$)$_2$, N(R$^9$)$_3$L or CO$_2$R$^9$; wherein each R$^9$ is independently selected from H or alkyl; and L is a counter ion;
R$^6$ is H or alkyl;
R$^7$ is H, alkyl or CO$_2$R$^{10}$; wherein R$^{10}$ is alkyl;
or a pharmaceutically acceptable salt or prodrug thereof, wherein said prodrug has a terminal group selected from an ester derivative, an amide derivative and a peptide,
with the proviso that when Z is H, then X$^1$ and X$^2$ cannot both be C=O while Y$^1$ is (CH$_2$)$_p$ with p=0, while Y$^2$ is (CH$_2$)$_q$ with q=0, and while R$^1$ and R$^2$ are both methyl.

2. A pound having potassium channel inhibitory activity of the formula:

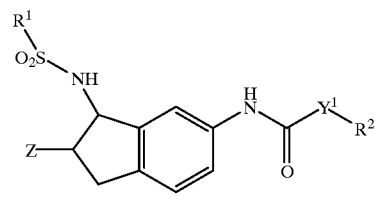

wherein,
R$^1$ is selected from the group of an optionally substituted aryl and an optionally substituted heteroaryl;
R$^2$ is selected from the group of an optionally substituted aryl and an optionally substituted heteroaryl;
Y$^1$ is O, (CH$_2$)$_p$, CH$_2$O, HC=CH or NH; wherein p is 0, 1 or 2; and
Z is H or OR$^5$, wherein R$^5$ is H (CH$_2$)$_m$—R$^8$; or C(O)—(CH$_2$)$_m$—R$^8$; m=1 to 5; R$^8$ is N(R$^9$)$_2$, N(R$^9$)$_3$L or CO$_2$R$^9$; wherein each R$^9$ is independently selected from H or alkyl; and L is a counter ion;
or a pharmaceutically acceptable salt or prodrug thereof, wherein said prodrug has a terminal group selected from an ester derivative, an amide derivative and a peptide.

3. A compound having potassium channel inhibitory activity of the formula:

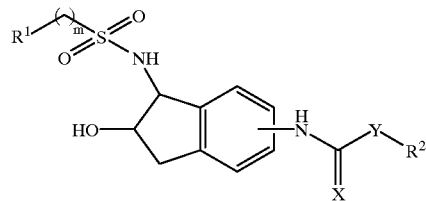

wherein,
R$^1$ is H or an optionally substituted aryl selected from the group of phenyl and β-naphthyl;
R$^2$ is selected from the group of an optionally substituted phenyl, an optionally substituted heterocyclyl, an optionally substituted heteroaryl and an optionally substituted carbocycloalkyl;
m is 0 or 1;
X is O or S ; and
Y is selected from one of (CH$_2$)$_p$, (CH$_2$O)$_q$ and (NH)$_r$; where p is 0, 1 or 2; q is 0 or 1, and r is 0 O or 1;
or a pharmaceutically acceptable salt or prodrug thereof, wherein said prodrug has a terminal group selected from an ester derivative, an amide derivative and a peptide.

4. A compound according to claim 3 having the formula:

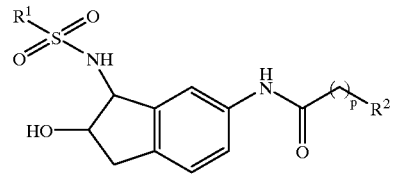

wherein R$^1$, R$^2$ and p have the same meanings recited in claim 3;

or a pharmaceutically acceptable salt or prodrug thereof, wherein said prodrug has a terminal group selected from an ester derivative, an amide derivative and a peptide.

5. A pharmaceutical composition comprising a compound of the following formula:

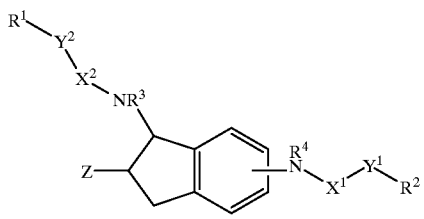

wherein
- R¹ is H, alkyl or is selected from the group consisting of an optionally substituted aryl, an optionally substituted heteroaryl, an optionally substituted heterocyclyl and an optionally substituted carbocycloalkyl;
- R² is selected from the group consisting of alkyl, an optionally substituted aryl, an optionally substituted heteroaryl, an optionally substituted heterocyclyl and an optionally substituted carbocycloalkyl;
- R³ is hydrogen or methyl;
- R⁴ is hydrogen or methyl;
- X¹ is C=O, C=S, or SO₂;
- X² is C=O or SO₂;
- Y¹ is O, (CH₂)$_p$, CH₂O, HC=CH or NH; wherein p is 0, 1 or 2;
- Y² is O, (CH₂)$_q$, HC=CH or NH; wherein q is 0 or 1;
- Z is H, OR⁵ or NR⁶R⁷;
wherein
- R⁵ is H, (CH₂)$_m$—R⁸; or C(O)—(CH₂)$_m$—R⁸; m=1 to 5;
- R⁸ is N(R⁹)₂, N(R⁹)₃L or CO₂R⁹; wherein each R⁹ is independently selected from H or alkyl; and L is a counter ion;
- R⁶ is H or alkyl;
- R⁷ is H, alkyl or CO₂R¹⁰; wherein R¹⁰ is alkyl;

or a pharmaceutically acceptable salt or prodrug thereof; wherein said prodrug has a terminal group selected from an ester derivative, an amide derivative and a peptide, and a pharmaceutically acceptable diluent or carrier with the proviso that when Z is H, then X¹ and X² cannot both be C=O while Y¹ is (CH₂)$_p$ with p=0, while Y² is (CH₂)$_q$ with q=0, and while R¹ and R² are both methyl.

6. A pharmaceutical composition comprising a compound of the following formula:

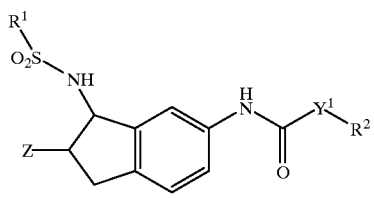

wherein,
- R¹ is selected from the group of an optionally substituted aryl and an optionally substituted heteroaryl;
- R² is selected from the group of an optionally substituted aryl and an optionally substituted heteroaryl;
- Y¹ is O, (CH₂)$_p$, CH₂O, HC=CH or NH; wherein p is 0, 1 or 2; and
- Z is H or OR⁵, wherein R⁵ is H, (CH₂)$_m$—R⁸; or C(O)—(CH₂)$_m$—R⁸; m=1 to 5; R⁸ is N(R⁹)₂, N(R⁹)₃L or CO₂R⁹; wherein each R⁹ is independently selected from H or alkyl; and L is a counter ion, or a pharmaceutically acceptable salt or prodrug thereof; wherein said prodrug has a terminal group selected from an ester derivative, an amide derivative and a peptide, and a pharmaceutically acceptable diluent or carrier.

7. A pharmaceutical composition comprising a compound of the following formula:

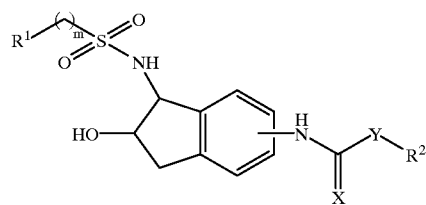

wherein,
- R¹ is H or an optionally substituted aryl selected from the group of phenyl and β-naphthyl;
- R² is selected from the group of an optionally substituted phenyl, an optionally substituted heterocyclyl and an optionally substituted carbocycloalkyl;
- m is 0 or 1;
- X is O or S; and
- Y is selected from one of (CH₂)$_p$, (CH₂O)$_q$ and (NH)$_r$; where p is 0, 1 or 2; q is 0 or 1, and r is 0 or 1;

or a pharmaceutically acceptable salt or prodrug thereof; wherein said prodrug has a terminal group selected from an ester derivative, an amide derivative and a peptide, and a pharmaceutically acceptable diluent or carrier.

8. A pharmaceutical composition comprising a compound of the following formula:

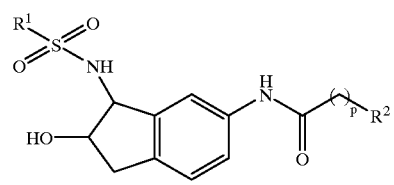

wherein R¹, R², m and p have the meanings recited in claim 7;

or a pharmaceutically acceptable salt or prodrug thereof, wherein said prodrug has a terminal group selected from an ester derivative, an amide derivative and a peptide, and a pharmaceutically acceptable diluent or carrier.

9. A method for inhibiting potassium transport across cellular membranes possessing potassium channels comprising exposing a cell membrane possessing said channels to the presence of a compound of the formula:

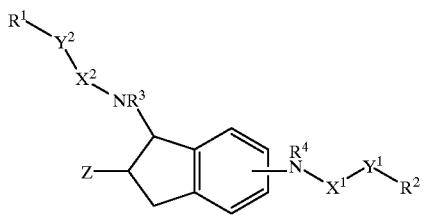

wherein,
- $R^1$ is H, alkyl or is selected from the group consisting of an optionally substituted aryl, an optionally substituted heteroaryl, an optionally substituted heterocyclyl and an optionally substituted carbocycloalkyl;
- $R^2$ is selected from the group consisting of alkyl, an optionally substituted aryl, an optionally substituted heteroaryl, an optionally substituted heterocyclyl and an optionally substituted carbocycloalkyl;
- $R^3$ is hydrogen or methyl;
- $R^4$ is hydrogen or methyl;
- $X^1$ is C=O, C=S, or $SO_2$;
- $X^2$ is C=O or $SO_2$;
- $Y^1$ is O, $(CH_2)_p$, $CH_2O$, HC=CH or NH; wherein p is 0, 1 or 2;
- $Y^2$ is O, $(CH_2)_q$, HC=CH or NH; wherein q is 0 or 1;
- Z is H, $OR^5$ or $NR^6R^7$;
wherein
- $R^5$ is H, $(CH_2)_m$—$R^8$; or C(O)—$(CH_2)_m$—$R^8$; m=1 to 5;
- $R^8$ is $N(R^9)_2$, $N(R^9)_3L$ or $CO_2R^9$; wherein each $R^9$ is independently selected from H or alkyl; and L is a counter ion;
- $R^6$ is H or alkyl;
- $R^7$ is H, alkyl or $CO_2R^{10}$; wherein $R^{10}$ is alkyl;
- or a pharmaceutically acceptable salt or prodrug thereof, said compound being present in an amount effective to block conductance of said channels.

10. The method of claim 9 wherein the potassium channel is a voltage gated potassium channel.

11. The method of claim 10 wherein the potassium channel is selected from a potassium channel responsible for cardiac $I_{Kur}$ potassium current, a potassium channel responsible for T-lymphocyte $I_{Kn}$ potassium current and potassium channels containing one of Kv1.5 or Kv1.3 α-subunit gene products.

12. A method for inhibiting potassium transport across cellular membranes possessing potassium channels comprising exposing a cell membrane possessing said channels to the presence of a compound of the formula:

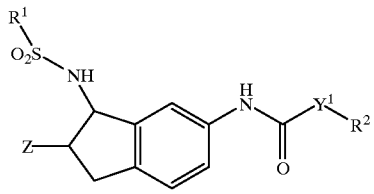

wherein
- $R^1$ is selected from the group of an optionally substituted aryl and an optionally substituted heteroaryl;
- $R^2$ is selected from the group of an optionally substituted aryl and an optionally substituted heteroaryl;
- $Y^1$ is O, $(CH_2)_p$, $CH_2O$, HC=CH or NH; wherein p is 0, 1 or 2; and
- Z is H or $OR^5$, wherein $R^5$ is H, $(CH_2)_m$—$R^8$; or C(O)—$(CH_2)_m$—$R^8$; m=1 to 5; $R^8$ is $N(R^9)_2$, $N(R^9)_3L$ or $CO_2R^9$; wherein each $R^9$ is independently selected from H or alkyl; and L is a counter ion;
- or a pharmaceutically acceptable salt or prodrug thereof, said compound being present in an amount effective to block conductance of said channels.

13. The method of claim 12 wherein the potassium channel is a voltage gated potassium channel.

14. The method of claim 13 wherein the potassium channel is selected from a potassium channel responsible for cardiac $I_{Kur}$ potassium current, a potassium channel responsible for T-lymphocyte $I_{Kn}$ potassium current and potassium channels containing one of Kv1.5 or Kv1.3 α-subunit gene products.

15. A method for inhibiting potassium transport across cellular membranes possessing potassium channels comprising exposing a cell membrane possessing said channels to the presence of a compound of the formula:

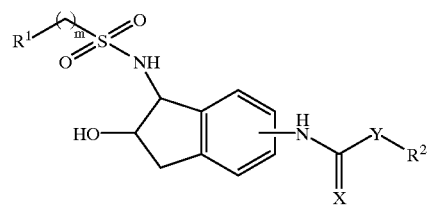

wherein,
- $R^1$ is H or an optionally substituted aryl selected from the group of phenyl and β-naphthyl;
- $R^2$ is selected from the group of an optionally substituted phenyl, an optionally substituted heterocyclyl and an optionally substituted carbocycloalkyl;
- m is 0 or 1;
- X is O or S; and
- Y is selected from one of $(CH_2)_p$, $(CH_2O)_q$ and $(NH)_r$; where p is 0, 1 or 2; q is 0 or 1, and r is 0 or 1;
- or a pharmaceutically acceptable salt or prodrug thereof;

said compound being present in an amount effective to block conductance of said channels.

16. The method of claim 15 wherein the potassium channel is a voltage gated potassium channel.

17. The method of claim 16 wherein the potassium channel is selected from a potassium channel responsible for cardiac $I_{Kur}$ potassium current, a potassium channel responsible for T-lymphocyte $I_{Kn}$ potassium current and potassium channels containing one of Kv1.5 or Kv1.3 α-subunit gene products.

18. A method for treating cardiac arrhythmias which comprises administering to a patient in need thereof, a pharmaceutically effective amount of a compound of the following formula:

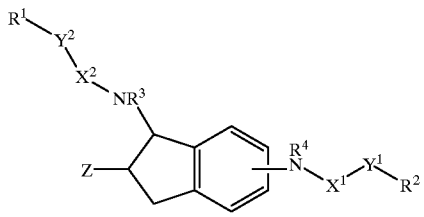

wherein,
R¹ is H, alkyl or is selected from the group consisting of an optionally substituted aryl, an optionally substituted heteroaryl, an optionally substituted heterocyclyl and an optionally substituted carbocycloalkyl;

R² is selected from the group consisting of alkyl an optionally substituted aryl, an optionally substituted heteroaryl, an optionally substituted heterocyclyl and an optionally substituted carbocycloalkyl;

R³ is hydrogen or methyl;

R⁴ is hydrogen or methyl;

X¹ is C=O, C=S, or SO₂;

X² is C=O or SO₂;

Y¹ is O, $(CH_2)_p$, $CH_2O$, HC=CH or NH; wherein p is 0, 1 or 2;

Y² is O, $(CH_2)_q$, HC=CH or NH; wherein q is 0 or 1;

Z is H, OR⁵ or NR⁶R⁷;

wherein

R⁵ is H, $(CH_2)_m$—R⁸; or C(O)—$(CH_2)_m$—R⁸;

m=1 to 5;

R⁸ is $N(R^9)_2$, $N(R^9)_3L$ or $CO_2R^9$; wherein each R⁹ is independently selected from H or alkyl; and L is a counter ion;

R⁶ is H or alkyl;

R⁷ is H; alkyl or $CO_2R^{10}$; wherein R¹⁰ is alkyl;

or a pharmaceutically acceptable salt or prodrug thereof, wherein said prodrug has a terminal group selected from an ester derivative, an amide derivative and a peptide.

19. A method for treating a cell proliferative disorder which comprises administering to a patient in need thereof, a pharmaceutically effective amount of a compound of the following formula:

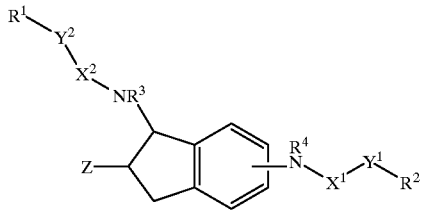

wherein,
R¹ is H, alkyl or is selected from the group consisting of an optionally substituted aryl, an optionally substituted heteroaryl, an optionally substituted heterocyclyl and an optionally substituted carbocycloalkyl;

R² is selected from the group consisting of alkyl, an optionally substituted aryl, an optionally substituted heteroaryl, an optionally substituted heterocyclyl and an optionally substituted carbocycloalkyl;

R³ is hydrogen or methyl;

R⁴ is hydrogen or methyl;

X¹ is C=O, C=S, or SO₂;

X² is C=O or SO₂;

Y¹ is O, $(CH_2)_p$, $CH_2O$, HC=CH or NH; wherein p is 0, 1 or 2;

Y² is O, $(CH_2)_q$, HC=CH or NH; wherein q is 0 or 1;

Z is H, OR⁵ or NR⁶R⁷;

wherein

R⁵ is H, $(CH_2)_m$—R⁸; or C(O)—$(CH_2)_m$—R⁸;

m=1 to 5;

R⁸ is $N(R^9)_2$, $N(R^9)_3L$ or $CO_2R^9$; wherein each R⁹ is independently selected from H or alkyl; and L is a counter ion;

R⁶ is H or alkyl;

R⁷ is H, alkyl or $CO_2R^{10}$; wherein R¹⁰ is alkyl;

or a pharmaceutically acceptable salt or prodrug thereof.

20. A method for treating cardiac arrhythmias which comprises administering to a patient in need thereof, a pharmaceutically effective amount of a compound of the following formula:

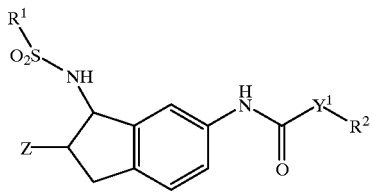

wherein,
R¹ is selected from the group of an optionally substituted aryl and an optionally substituted heteroaryl;

R² is selected from the group of an optionally substituted aryl and an optionally substituted heteroaryl;

Y¹ is O, $(CH_2)_p$, $CH_2O$, HC=CH or NH; wherein p is 0, 1 or 2; and

Z is H or OR⁵, wherein R⁵ is H, $(CH_2)_m$—R⁸; or C(O)—$(CH_2)_m$—R⁸; m=1 to 5; R⁸ is $N(R^9)_2$, $N(R^9)_3L$ or $CO_2R^9$; wherein each R⁹ is independently selected from H or alkyl; and L is a counter ion or a pharmaceutically acceptable salt or prodrug thereof, wherein said prodrug has a terminal group selected from an ester derivative, an amide derivative and a peptide.

21. A method for treating a cell proliferative disorder which comprises administering to a patient in need thereof, a pharmaceutically effective amount of a compound of the formula:

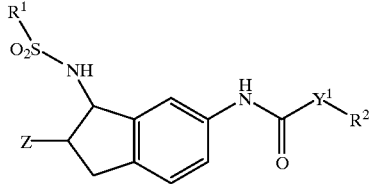

wherein,
R¹ is selected from the group of an optionally substituted aryl and an optionally substituted heteroaryl;

R² is selected from the group of an optionally substituted aryl and an optionally substituted heteroaryl;

Y¹ is O, $(CH_2)_p$, $CH_2O$, HC=CH or NH; wherein p is 0, 1 or 2; and

Z is H or OR⁵, wherein R⁵ is H, $(CH_2)_m$—R⁸; or C(O)—$(CH_2)_m$—R⁸; m=1 to 5; R⁸ is $N(R^9)_2$, $N(R^9)_3L$ or $CO_2R^9$; wherein each R⁹ is independently selected from H or alkyl; and L is a counter ion or a pharmaceutically acceptable salt or prodrug thereof.

22. A method for treating cardiac arrhythmias which comprises administering to a patient in need thereof, a pharmaceutically effective amount of a compound of the following formula

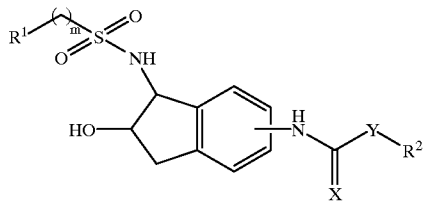

wherein,
- R¹ is H or an optionally substituted aryl selected from the group of phenyl and β-naphthyl;
- R² is selected from the group of an optionally substituted phenyl, an optionally substituted heterocyclyl and an optionally substituted carbocycloalkyl;
- m is O0 or 1;
- X is O or S; and
- Y is selected from one of $(CH_2)_p$, $(CH_2O)_q$ and $(NH)_r$; where p is 0, 1 or 2; q is 0 or 1, and r is 0 or 1;

or a pharmaceutically acceptable salt or prodrug thereof, wherein said prodrug has a terminal group selected from an ester derivative, an amide derivative and a peptide.

23. A method for treating a cell proliferative disorder which comprises administering to a patient in need thereof, a pharmaceutically effective amount of a compound of the following formula:

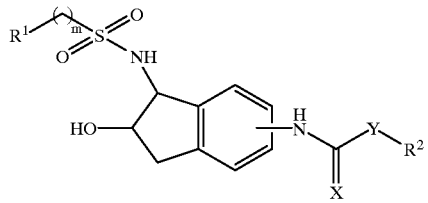

wherein,
- R¹ is H or an optionally substituted aryl selected from the group of phenyl and β-naphthyl;
- R² is selected from the group of an optionally substituted phenyl, an optionally substituted heterocyclyl and an optionally substituted carbocycloalkyl;
- m is 0 or 1;
- X is O or S ;and
- Y is selected from one of $(CH_2)_p$, $(CH_2O)_q$ and $(NH)_r$; where p is 0, 1 or 2; q is 0 or 1, and r is 0 or 1;

or a pharmaceutically acceptable salt or prodrug thereof.

* * * * *

UNITED STATES PATENT AND TRADEMARK OFFICE
CERTIFICATE OF CORRECTION

PATENT NO. : 6,083,986
DATED : July 4, 2000
INVENTOR(S) : Neil Alexander Castle et al.

Page 1 of 1

It is certified that error appears in the above-identified patent and that said Letters Patent is hereby corrected as shown below:

Claim 3, Column 50:
Line 50: "0O" has been replaced with --0--.

Claim 21, Column 56:
Line 50: "formula" has been replaced with --following formula--.

Claim 22, Column 57:
Line 27: "0O" has been replaced with --0--.

Signed and Sealed this

Tenth Day of July, 2001

*Nicholas P. Godici*

Attest:

NICHOLAS P. GODICI
Attesting Officer  *Acting Director of the United States Patent and Trademark Office*